United States Patent [19]

Daniels et al.

[11] 4,212,859

[45] Jul. 15, 1980

[54] 2'-HYDROXY-2'-DESAMINO-4,6-DI-O-(AMINOGLYCOSYL)-1,3-DIAMINOCY-CLITOLS, METHODS FOR THEIR MANUFACTURE, METHOD FOR THEIR USE AS ANTIBACTERIAL AGENTS, AND COMPOSITIONS USEFUL THEREFOR

[75] Inventors: Peter J. L. Daniels, Cedar Grove; Stuart McCombie, West Orange; Tattanahalli L. Nagabhushan, Parsippany, all of N.J.

[73] Assignee: Schering Corporation, Kenilworth, N.J.

[21] Appl. No.: 912,603

[22] Filed: Jun. 5, 1978

Related U.S. Application Data

[63] Continuation-in-part of Ser. No. 809,839, Jun. 24, 1977, abandoned.

[51] Int. Cl.$^2$ .................. A61K 31/71; C07H 15/22
[52] U.S. Cl. ................................. 424/180; 536/10; 536/17 R
[58] Field of Search ............... 536/10, 17; 424/180

[56] References Cited

U.S. PATENT DOCUMENTS

| | | | |
|---|---|---|---|
| 3,828,021 | 8/1974 | Beattie et al. | 536/17 |
| 4,066,752 | 1/1978 | Mallams et al. | 536/17 |
| 4,085,208 | 4/1978 | Mallams et al. | 536/10 |

*Primary Examiner*—Johnnie R. Brown
*Attorney, Agent, or Firm*—Mary S. King

[57] ABSTRACT

2'-Hydroxy-2'-desamino-4,6-di-O-(aminoglycosyl)-1,3-diaminocyclitols having a 6'-amino function exhibit antibacterial activity and are prepared by reaction of the corresponding N-protected (except the 2'-amino)-4,6-di-O-(aminoglycosyl)-1,3-diaminocyclitol with hydrogen peroxide in the presence of tungstate ion, followed by cleavage of the thereby formed 2'-oximino derivative, thence reduction of the resulting 2'-oxo derivative and removal of the N-protecting groups.

Preferred compounds are 1-N-($\omega$-amino-$\alpha$-hydroxyalkanoyl)-2'-hydroxy-2'-desamino-4,6-di-O-(aminoglycosyl)-1,3-diaminocyclitols which exhibit antibacterial activity against bacteria resistant to the parent aminoglycoside.

20 Claims, No Drawings

2'-HYDROXY-2'-DESAMINO-4,6-DI-O-(AMINO-GLYCOSYL)-1,3-DIAMINOCYCLITOLS, METHODS FOR THEIR MANUFACTURE, METHOD FOR THEIR USE AS ANTIBACTERIAL AGENTS, AND COMPOSITIONS USEFUL THEREFOR

CROSS REFERENCE TO RELATED APPLICATIONS

This application is a continuation-in-part of our co-pending application Ser. No. 809,839 filed June 24, 1977, now abandoned.

FIELD OF INVENTION

This invention relates to novel compositions-of-matter, to methods for their manufacture, to pharmaceutical formulations thereof and to methods for their use as antibacterial agents.

More specifically, this invention relates to novel 2'-hydroxy-2'-desamino-4,6-di-O-(aminoglycosyl)-1,3-diaminocyclitols having a 6'-amino function and 1-N-substituted derivatives thereof having antibacterial activity, to pharmaceutical compositions thereof and to methods for their use in treating bacterial infections.

In particular, this invention relates to 2'-hydroxy-2'-desamino derivatives of gentamicins $C_1$, $C_{1a}$, $C_2$, $C_{2a}$, $C_{2b}$, sisomicin, verdamicin, tobramycin, Antibiotics G-52, 66-40B, 66-40D, JI-20B, 3',4'-dideoxykanamycin B, the 5-deoxy-, 5-epi-, 5-epi-azido-5-deoxy derivatives thereof; Antibiotics Mu-1 and Mu-4 and 1-N-alkyl and 1-N-(ω-amino-α-hydroxyalkanoyl) derivatives of the foregoing.

This invention also relates to the process for preparing said 2'-hydroxy-2'-desamino-4,6-di-O-(aminoglycosyl)-1,3-diaminocyclitols, to pharmaceutical compositions comprising said novel 2'-hydroxy-2'-desamino-4,6-di-O-(aminoglycosyl)-1,3-diaminocyclitols, and to the method of using said pharmaceutical compositions to elicit an antibacterial response in a warm-blooded animal having a susceptible bacterial infection.

PRIOR ART

Known in the art are broad spectrum antibacterial agents which may be classified chemically as 4,6-di-O-(aminoglycosyl)-1,3-diaminocyclitols. Of these, some microbiologically produced antibiotics (i.e. kanamycins A and B and gentamicins B and $B_1$) contain a 2'-hydroxy group and a 6'-amino function. Thus, gentamicins B and $B_1$ are coproduced with gentamicin C complex during the fermentation of certain species of the genus Micromonospora, e.g. M. purpurea NRRL 2953, as described in U.S. Pat. Nos. 3,091,572 and 3,915,955; and kanamycins A and B are produced microbiologically by the fermentation of certain species of the genus Streptomyces, e.g. S. kanamyceticus ATCC 12853 as described in U.S. Pat. No. 2,931,798.

By our invention, it is now possible to prepare via chemical means novel 2'-hydroxy-2'-desamino-4,6-di-O-(aminoglycosyl)-1,3-diaminocyclitol antibacterial agents which cannot be produced via prior art microbiological methods. For example, by our novel process, gentamicin $C_{1a}$ is converted to a novel antibacterial agent 2'-hydroxy-2'-desaminogentamicin $C_{1a}$ (which may also be named 3',4'-dideoxygentamicin B).

Our invention also provides an alternative method of preparing gentamicin B (which is obtained in poor yields, i.e. less than about 10%, when prepared microbiologically) by converting Antibiotic JI-20A to 2'-hydroxy-2'-desamino-Antibiotic JI-20A which has the same structure as gentamicin B.

GENERAL DESCRIPTION OF THE INVENTION COMPOSITION-OF-MATTER ASPECT

Included among the antibacterially active compositions-of-matter of this invention are 2'-hydroxy-2'-desamino-4,6-di-O-(aminoglycosyl)-1,3-diaminocyclitols having an amino function at C-6' selected from the group consisting of 2'-hydroxy-2'-desaminogentamicin $C_1$,
2'-hydroxy-2'-desaminogentamicin $C_{1a}$,
2'-hydroxy-2'-desaminogentamicin $C_2$,
2'-hydroxy-2'-desaminogentamicin $C_{2a}$,
2'-hydroxy-2'-desaminogentamicin $C_{2b}$,
2'-hydroxy-2'-desaminosisomicin,
2'-hydroxy-2'-desaminoverdamicin,
2'-hydroxy-2'-desamino-Antibiotic G-52,
2'-hydroxy-2'-desamino-Antibiotic 66-40B,
2'-hydroxy-2'-desamino-Antibiotic 66-40D,
2'-hydroxy-2'-desamino-Antibiotic JI-20B,
2'-hydroxy-2'-desaminotobramycin; and
2'-hydroxy-2'-desamino-3',4'-dideoxykanamycin B;
the 5-deoxy-, 5-epi-, 5-epi-azido-5-deoxy- and the 5-epi-fluoro-5-deoxy derivatives thereof;
2'-hydroxy-2'-desamino-Antibiotic Mu-1, and
2'-hydroxy-2'-desamino-Antibiotic Mu-4;

the 1-N-(ω-amino-α-hydroxyalkanoyl) derivatives of the foregoing wherein said alkanoyl has from 3 to 5 carbon atoms, and the 1-N-X derivatives of the foregoing wherein X is a substituent selected from the group consisting of alkyl, cycloalkylalkyl, alkenyl, aralkyl, hydroxyalkyl, aminoalkyl, alkylaminoalkyl, aminohydroxyalkyl, and alkylaminohydroxyalkyl, said substituent having up to 8 carbon atoms, the carbon in said substituent adjacent to the aminoglycoside nitrogen being unsubstituted, and when said substituent is substituted by both hydroxyl and amino functions, only one of said functions can be attached at any one carbon atom; and the pharmaceutically acceptable acid addition salts thereof.

Included among the substituents contemplated for the moiety "X" in our novel compounds are straight and branched chain alkyl groups such as ethyl, n-propyl, n-butyl, β-methylpropyl, n-pentyl, β-methylbutyl, γ-methylbutyl and β,β-dimethylpropyl, n-hexyl, δ-methylpentyl, β-ethylbutyl, γ-ethylbutyl, n-heptyl, ε-methylheptyl, β-ethylpentyl, γ-ethylpentyl, δ-ethylpentyl, γ-propylbutyl, n-octyl, iso-octyl, β-ethylhexyl, δ-ethylhexyl, ε-ethylhexyl, β-propylpentyl, γ-propylpentyl; cycloalkylalkyl groups groups such as cyclopropylmethyl, cyclopentylmethyl, cyclohexylmethyl and cyclopentylethyl; alkenyl groups such as β-propenyl, β-methylpropenyl, β-butenyl, β-methyl-β-butenyl, β-ethyl-β-hexenyl: aralkyl groups such as benzyl, o-tolyl, m-tolyl, p-tolyl and phenylethyl: hydroxy substituted straight and branched chain alkyl groups such as ε-hydroxypentyl, β-hydroxy-γ-methylbutyl, β-hydroxy-β-methylpropyl, δ-hydroxybutyl, β-hydroxypropyl, γ-hydroxypropyl, ω-hydroxyoctyl; amino substituted straight and branched chain alkyl groups such as ε-aminopentyl, β-aminopropyl, γ-aminopropyl, δ-aminobutyl, β-amino-γ-methylbutyl and ω-aminooctyl and mono-N-alkylated derivatives thereof such as the N-methyl, N-ethyl, and N-propyl derivatives, e.g. ε-methylaminopentyl, β-methylaminopropyl, β-ethylaminopropyl, δ-methylaminobutyl, β-methylamino-γ-methylbutyl, and ω-methylaminobutyl: amino and hydroxy disubstituted straight and branched chain alkyl groups such as β-hydroxy-ε-aminopentyl, γ-hydroxy-γ-methyl-δ-aminobutyl, β-hydroxy-δ-aminobutyl, β-hydroxy-γ-aminopropyl, and β-hydroxy-β-methyl-γ-aminopropyl: and mono-N-alkylated derivatives thereof such as β-hydroxy-ε-methylaminopentyl, γ-hydroxy-γ-methyl-δ-methylaminobutyl, β-hydroxy-δ-methylaminobutyl, β-hydroxy-γ-ethylaminopropyl, and β-hydroxy-β-methyl-γ-methyl aminopropyl.

Of the foregoing substituents for the moiety "X", preferred are ethyl, n-propyl and δ-aminobutyl.

Particularly useful antibacterial agents of our invention include 2'-hydroxy-2'-desamino-4,6-di-O-(aminoglycosyl)-1,3-diaminocyclitols having a 6'-amino function wherein said 1,3-diaminocyclitol is 2-deoxystreptamine, (e.g. 2'-hydroxy-2'-desaminotobramycin, 2'-hydroxy-2'-desamino-3',4'-dideoxykanamycin B and 2'-hydroxy-2'-desamino-Antibiotics 66-40B and 66-40D), particularly those compounds wherein said 6-O-aminoglycosyl is 6-O-garosaminyl, including 2'-hydroxy-2'-desamino derivatives of gentamicins $C_1$, $C_{1a}$, $C_2$, $C_{2a}$, $C_{2b}$, Antibiotics G-52 and JI-20B, sisomicin and verdamicin. Of the latter, particularly preferred are derivatives having a primary carbinamine at C-5', e.g. 2'-hydroxy-2'-desaminosisomicin and 2'-hydroxy-2'-desaminogentamicin $C_{1a}$ (also named 3',4'-dideoxygentamicin B).

Of the 1-N-substituted derivatives of our invention, preferred are the 1-N-(ω-amino-α-hydroxyalkanoyl)-2'-hydroxy-2'-desamino-4,6-di-O-(aminoglycosyl)-1,3-diaminocyclitols, particularly the 1-N-(γ-amino-α-hydroxybutyryl) and the 1-N-(β-amino-α-hydroxypropionyl) derivatives, particularly valuable compounds being 1-N-(S-γ-amino-α-hydroxybutyryl)-2'-hydroxy-2'-desaminogentamicin $C_{1a}$ and 1-N-(S-β-amino-α-hydroxypropionyl)-2'-hydroxy-2'-desaminogentamicin $C_{1a}$.

It is to be noted that the 1-N-(ω-amino-α-hydroxyalkanoyl) substituent in the foregoing 1-N-(ω-amino-α-hydroxyalkanoyl)-2'-hydroxy-2'-desamino-4,6-di-O-(aminoglycosyl)-1,3-diaminocyclitols may be in the R,S— form or in the R— form or in the S— form. In accordance with this invention, each of the foregoing names includes all three forms. Thus, the name 1-N-(γ-amino-α-hydroxybutyryl)-2'-hydroxy-2'-desaminogentamicin $C_{1a}$ includes 1-N-(S-γ-amino-α-hydroxybutyryl)-2'-hydroxy-2'-desaminogentamicin $C_{1a}$, 1-N-(R-γ-amino-α-hydroxybutyryl)-2'-hydroxy-2'-desaminogentamicin $C_{1a}$ and 1-N-(R,S-γ-amino-α-hydroxybutyryl)-2'-hydroxy-2'-desaminogentamicin $C_{1a}$.

Also included within the composition-of-matter aspect of this invention are pharmaceutically acceptable acid addition salts of the 2'-hydroxy-2'-desamino-4,6-di-O-(aminoglycosyl)-1,3-diaminocyclitols of this invention, which salts are made according to known procedures such as by neutralizing the free base with the appropriate acid, usually to about pH 5. Suitable acids for this purpose include acids such as hydrochloric, sulfuric, phosphoric, hydrobromic and the like. The physical embodiments of the acid addition salts of the 2'-hydroxy-2'-desamino-4,6-di-O-(aminoglycosyl)-1,3-diaminocyclitols are characterized by being white solids which are soluble in water and insoluble in most polar and non-polar organic solvents.

The 2'-hydroxy-2'-desamino-4,6-di-O-(aminoglycosyl)-1,3-diaminocyclitols of this invention (particularly those wherein the 6-O-aminoglycosyl is 6-O-garosaminyl and wherein the 1,3-diaminocyclitol is 2-deoxystreptamine) and their non-toxic, pharmaceutically acceptable acid addition salts, in general, exhibit broad spectrum antibacterial activity and possess an improved antibacterial spectrum compared to that of the parent antibiotics. This improved spectrum consists of enhanced potency of the claimed compounds against organisms resistant to the parent compound. Thus, for example, compounds of this invention, e.g. 2'-hydroxy-2'-desamino-4-O-aminoglycosyl-6-O-garosaminyl-2-deoxystreptamines, are more active against organisms which inactivate the parent antibiotics by acetylation of the 2'-amino group. In addition to the foregoing, the 2'-hydroxy-2'-desamino-4,6-di-O-(aminoglycosyl)-1,3-diaminocyclitols and their non-toxic, pharmaceutically acceptable acid addition salts are, in general, less acutely toxic than their precursor 2'-amino parent antibiotics.

Particularly valuable are 2'-hydroxy-2'-desaminogentamicin $C_1$ and 2'-hydroxy-2'-desaminogentamicin $C_{1a}$, which derivatives are broad spectrum antibacterial agents, being active against gram positive bacteria (e.g. *Staphylococcus aureus*) and gram negative bacteria (e.g., *Escherichia coli* and *Pseudomonas aeruginosa*) as determined by standard dilution tests, including bacteria resistant to the parent compound.

Most valuable compounds of this invention are the 1-N-(ω-amino-α-hydroxyalkanoyl) derivatives of 2'-hydroxy-2'-desamino-gentamicin $C_{1a}$, particularly 1-N-(S-γ-amino-α-hydroxybutyryl) 2'-hydroxy-2'-desaminogentamicin $C_{1a}$ and 1-N-(S-β-amino-α-hydroxypropionyl)-2'-hydroxy-2'-desaminogentamicin $C_{1a}$ which exhibit broader spectra of antibacterial activity than the precursor 1-N-unsubstituted-2'-hydroxy-2'-desaminogentamicin $C_{1a}$ or the corresponding 1-N-(S-ω-amino-α-hydroxyalkanoyl) gentamicin $C_{1a}$. These preferred compounds possess improved potency versus bacteria resistant to the aforementioned precursor compounds, being active against 2"-adenylating and 3-acetylating strains of bacteria. Additionally, the foregoing 1-N-(ω-amino-α-hydroxyalkanoyl) derivatives of 2'-hydroxy-2'-desaminogentamicin $C_{1a}$ are advantageously less acutely toxic than the corresponding 1-N-(ω-amino-α-hydroxyalkanoyl)gentamicin $C_{1a}$.

GENERAL DESCRIPTION OF PHARMACEUTICAL COMPOSITION AND METHOD-OF-USE ASPECTS OF THE INVENTION

The present invention includes within its scope pharmaceutical compositions comprising our novel 2'-hydroxy-2'-desamino-4,6-di-O-(aminoglycosyl)-1,3-diaminocyclitols with a compatible, pharmaceutically acceptable carrier or coating. Also included within our invention is the method of eliciting an antibacterial response in a warm-blooded animal having a susceptible bacterial infection which comprises administering to said animal a non-toxic, antibacterially effective amount of a member selected from the group consisting of 2'-hydroxy-2'-desaminogentamicin $C_1$,
2'-hydroxy-2'-desaminogentamicin $C_{1a}$, 2'-hydroxy-2'-desaminogentamicin $C_2$,
2'-hydroxy-2'-desaminogentamicin $C_{2a}$,
2'-hydroxy-2'-desaminogentamicin $C_{2b}$,
2'-hydroxy-2'-desaminosisomicin,
2'-hydroxy-2'-desaminoverdamicin,
2'-hydroxy-2'-desamino-Antibiotic G-52,
2'-hydroxy-2'-desamino-Antibiotic 66-40B,
2'-hydroxy-2'-desamino-Antibiotic 66-40D,
2'-hydroxy-2'-desamino-Antibiotic JI-20B,
2'-hydroxy-2'-desaminotobramycin; and
2'-hydroxy-2'-desamino-3',4'-dideoxykanamycin B (which may also be named 3',4'-dideoxykanamycin A);
the 5-deoxy-, 5-epi-, 5-epi-azido-5-deoxy- and the 5-epi-fluoro-5-deoxy derivatives thereof;
2'-hydroxy-2'-desamino-Antibiotic Mu-1, and
2'-hydroxy-2'-desamino-Antibiotic Mu-4;

the 1-N-($\omega$-amino-$\alpha$-hydroxyalkanoyl) derivatives of the foregoing wherein said alkanoyl has from 3 to 5 carbon atoms, and the 1-N-X derivatives of the foregoing wherein X is a substituent selected from the group consisting of alkyl, cycloalkylalkyl, alkenyl, aralkyl, hydroxyalkyl, aminoalkyl, alkylaminoalkyl, aminohydroxyalkyl, and alkylaminohydroxyalkyl, said substituent having up to 8 carbon atoms, the carbon in said substituent adjacent to the aminoglycoside nitrogen being unsubstituted, and when said substituent is substituted by both hydroxyl and amino functions, only one of said functions can be attached at any one carbon atom; and the pharmaceutically acceptable acid addition salts thereof.

As discussed hereinabove, the 2'-hydroxy-2'-desamino-4,6-di-O-(aminoglycosyl)-1,3-diaminocyclitols of this invention and the non-toxic, pharmaceutically acceptable acid addition salts thereof, are broad spectrum antibacterial agents which, advantageously, exhibit activity against organisms which are resistant to their 2'-amino precursors. Thus, the 2'-hydroxy-2'-desamino compounds of this invention can be used alone or in combination with other antibiotic agents to prevent the growth or reduce the number of bacteria in various environments. They may be used, for example, to disinfect laboratory glassware, dental and medical equipment contaminated with *Staphylococcus aureus* or other bacteria inhibited by the 2'-hydroxy-2'-desamino derivatives of this invention.

The activity of the 2'-hydroxy-2'-desamino-4,6-di-O-(aminoglycosyl)-1,3-diaminocyclitols against gram negative bacteria renders them useful for combating infections caused by gram negative organisms, e.g. species of Proteus and Pseudomonas. The 2'-hydroxy-2'-desamino-4,6-di-O-(aminoglycosyl)-1,3-diaminocyclitols, e.g. 1-N-(S-$\gamma$-amino-$\alpha$-hydroxybutyryl)-2'-hydroxy-2'-desaminogentamicin $C_{1a}$ and 1-N-(S-$\beta$-amino-$\alpha$-hydroxypropionyl)-2'-hydroxy-2'-desaminogentamicin $C_{1a}$, have veterinary applications, particularly in the treatment of mastitis in cattle and Salmonella-induced diarrhea in domestic animals such as the dog and the cat.

The dosage administered of the 2'-hydroxy-2'-desamino-4,6-di-O-(aminoglycosyl)-1,3-diaminocyclitols will be dependent upon the age and weight of the animal species being treated, the mode of administration, and the type and severity of bacterial infection being prevented or reduced. In general, the dosage of 2'-hydroxy-2'-desamino-4,6-di-O-(aminoglycosyl)-1,3-diaminocyclitol employed to combat a given bacterial infection will be similar to the dosage requirements of the corresponding 4,6-di-O-(aminoglycosyl)-1,3-diaminocyclitol. Additionally, many of the 2'-hydroxy-2'-desamino-4,6-di-O-(aminoglycosyl)-1,3-diaminocyclitols are also advantageously cidal against certain gram negative organisms which are resistant to the 2'-amino precursors.

The 2'-hydroxy-2'-desamino-4,6-di-O-(aminoglycosyl)-1,3-diaminocyclitols, preferably the 1-N-($\gamma$-amino-$\alpha$-hydroxybutyryl)- and the 1-N-($\beta$-amino-$\alpha$-hydroxypropionyl) derivatives of this invention, and the pharmaceutically acceptable acid addition salts thereof may be administered orally. They may also be applied topically in the form of ointments, both hydrophilic and hydrophobic, in the form of lotions which may be aqueous, non-aqueous or of the emulsion type or in the form of creams. Pharmaceutical carriers useful in the preparation of such formulations will include, for example, such substances as water, oils, greases, polyesters, polyols and the like.

For oral administration, the 2'-hydroxy-2'-desamino-4,6-di-O-(aminoglycosyl)-1,3-diaminocyclitol antibacterials, particularly the 1-N-($\omega$-amino-$\alpha$-hydroxyalkanoyl) derivatives of this invention may be compounded in the form of tablets, capsules, elixirs or the like or may even be admixed with animal feed. It is in these dosage forms that the antibacterials are most effective for treating bacterial infections of the gastrointestinal tract, which infections cause diarrhea.

In general, the topical preparations will contain from about 0.1 to about 3.0 gms. of a 2'-hydroxy-2'-desamino-4,6-di-O-(aminoglycosyl)-1,3-diaminocyclitol derivative per 100 gms. of ointment, creams or lotion. The topical preparations are usually applied gently to lesions from about 2 to about 5 times a day.

The antibacterials of this invention may be utilized in liquid form such as solutions, suspensions and the like for otic and optic use and may also be administered parenterally via intramuscular injection. The injectable solution or suspension will usually be administered at from about 1 mg. to about 10 mgs. of antibacterial per kilogram of body weight per day divided into about 2 to about 4 doses. The precise dose depends on the stage and severity of the infection, the susceptibility of the infecting organism to the antibacterial and the individual characteristics of the animal species being treated.

The following formulations are to exemplify some of the dosage forms in which the antibacterial agents of this invention and their derivatives may be employed.

| Tablet | Formulation 1 | | |
|---|---|---|---|
| | 10 mg. Tab. | 25 mg. Tab. | 100 mg. Tab. |
| 1-N-(S-$\gamma$-amino-$\alpha$-hydroxybutyryl)-2'-hydroxy-2'-desaminogentamicin $C_{1a}$ | 10.5* mg. | 26.25* mg. | 105.0* mg. |
| Lactose, impalpable powder | 197.50 mg. | 171.25 mg. | 126.00 mg. |
| Corn starch | 25.00 mg. | 25.00 mg. | 35.00 mg. |
| Polyvinylpyrrolidone | 7.50 mg. | 7.50 mg. | 7.50 mg. |
| Magnesium Stearate | 2.50 mg. | 2.50 mg. | 3.50 mg. |

*5% excess

Procedure

Prepare a slurry consisting of the 1-N-(S-$\gamma$-amino-$\alpha$-hydroxybutyryl)-2'-hydroxy-2'-desaminogentamicin $C_{1a}$, lactose and polyvinylpyrrolidone. Spray dry the slurry. Add the corn starch and magnesium stearate. Mix and compress into tablets.

| Formulation 2 | |
|---|---|
| Ointment | |
| 1-N-(S-γ-amino-α-hydroxybutyryl)-2'-hydroxy-2'-desaminogentamicin $C_{1a}$ | 1.9 gm. |
| Methylparaben, USP | 0.5 gm. |
| Propylparaben, USP | 0.1 gm. |
| Petrolatum | to 1000 gm. |

Procedure (1) Melt the petrolatum.

(2) Mix the 1-N-(S-γ-amino-α-hydroxybutyryl)-2'-hydroxy-2'-desaminogentamicin $C_{1a}$, methylparaben and propylparaben with about 10% of the molten petrolatum.

(3) Pass the mixture through a colloid mill.

(4) Add the remainder of the petrolatum with agitation and cool the mixture until it becomes semi-solid. At this stage the product may be put into suitable containers.

Ointments of other 2'-hydroxy-2'-desamino-4,6-di-O-(aminoglycosyl)-1,3-diaminocyclitols of this invention are prepared by substituting an equivalent quantity of 2'-hydroxy-2'-desamino-4,6-di-O-(aminoglycosyl)-1,3-diaminocyclitol or an acid addition salt thereof, for 1-N-(S-γ-amino-α-hydroxybutyryl)-2'-hydroxy-2'-desaminogentamicin $C_{1a}$ in the foregoing example and by following substantially the procedure of the example.

| Formulation 3 | | |
|---|---|---|
| Injectable Solution | Per 2.0 ml. Vial | Per 50 Liters |
| 1-N-(S-β-amino-α-hydroxypropionyl)-2'-hydroxy-2'-desaminogentamicin $C_{1a}$ | 84* mgs. | 2100* gms. |
| Methylparaben, USP | 3.6 mgs. | 90.0 gms. |
| Propylparaben, USP | 0.4 mgs. | 10.0 gms. |
| Sodium bisulfite, USP | 6.4 mgs. | 160.0 gms. |
| Disodium Ethylenediamine tetraacetate dihydrate, R.G. | 0.2 mgs. | 5.0 gms. |
| Water, USP q.s. | 2.0 ml. | 50.0 liters |

*Includes a 5% manufacturing overcharge

Procedure: For a 50.0 liter batch

Charge approximately 35 liters of water for injection to a suitable stainless steel jacketed vessel and heat to about 70° C. Charge the methylparaben and propylparaben to the heated water for injection and dissolve with agitation. When the parabens are completely dissolved, cool the contents of the tank to 25°–30° C. by circulating cold water through the tank jacket. Sparge the solution with nitrogen gas for at least 10 minutes and keep covered with nitrogen during subsequent processing. Charge and dissolve the disodium EDTA and sodium bisulfite. Charge and dissolve the 1-N-(S-β-amino-α-hydroxypropionyl)-2'-hydroxy-2'-desaminogentamicin $C_{1a}$ sulfate. Bring the batch volume up to 50.0 liters with water for injection and agitate until homogeneous.

Under sterile conditions, filter the solution through a suitable bacteria retentive filter collecting the filtrate in a filling tank.

Fill the filtrate aseptically into sterile pyrogen-free multiple dose vials, stopper and seal.

In like manner, injectable solutions of other 2'-hydroxy-2'-desamino-4,6-di-O-(aminoglycosyl)-1,3-diaminocyclitols and especially acid addition salts of such antibacterial agents, may be prepared by substituting an equivalent quantity of such compounds for 1-N-(S-β-amino-α-hydroxypropionyl)-2'-hydroxy-2'-desaminogentamicin $C_{1a}$ sulfate and by following the procedure set forth above.

GENERAL DESCRIPTION OF THE PROCESS ASPECT OF THE INVENTION

By the process of this invention, the 2'-amino function in a 4,6-di-O-(aminoglycosyl)-1,3-diaminocyclitol antibacterial agent having amino functions at the 2' and 6'-position, is converted to a hydroxyl function having the same stereochemistry at the 2'-position thereby producing the corresponding, antibacterially effective 2'-hydroxy-2'-desamino-4,6-di-O-(aminoglycosyl)-1,3-diaminocyclitol.

Specifically, our process comprises the reaction of a 4,6-di-O-(aminoglycosyl)-1,3-diaminocyclitol wherein said 4-O-aminoglycosyl has an amino function at the 2' and 6'-positions and said 6-O-aminoglycosyl has a hydroxyl group at the 2" and 4"-positions and a 3"-amino function, and wherein all amino functions except the 2'-amino function are protected by a protecting group, Y; with hydrogen peroxide in an aqueous lower alkanol in the presence of tungstate ion in a pH range of from about 9 to about 11, the molar quantity of hydrogen peroxide being at least twice the molar quantity of said 4,6-di-O-(aminoglycosyl)-1,3-diaminocyclitol; thence cleavage of the oxime function in the 2'-oximino-4,6-di-O-(aminoglycosyl)-1,3-diaminocyclitol thereby formed by reaction thereof with sodium bisulfite followed by mild acid hydrolysis or by reaction thereof in an acidic hydrolytic medium in the presence of acetaldehyde; followed by reaction of the resulting 2'-oxo-4,6-di-O-(aminoglycosyl)-1,3-diaminocyclitol with an alkali metal borohydride; thence removal of said protecting groups, Y, whereby is produced an antibacterially effective 2'-hydroxy-2'-desamino-4,6-di-O-(aminoglycosyl)-1,3-diaminoglyclitol.

In the first step of our process, the 2'-amino function in the N-protected (except at the 2'-position)-4,6-di-O-(aminoglycosyl)-1,3-diaminocyclitol starting compound is oxidized to an oxime function by reaction with hydrogen peroxide in a lower alkanol in the presence of catalytic quantities of tungstate ion in a pH range of from about 9 to 11. The reaction is continued until almost all the amino function is consumed as determined by thin layer chromatographic techniques, then the resulting 2'-oximino-N-protected-4,6-di-O-(aminoglycosyl)-1,3-diaminocyclitol intermediate is isolated as a mixture of syn and anti isomers utilizing known techniques (e.g. extraction and chromatographic techniques).

In carrying out this step of our process, it is necessary to use at least two moles of hydrogen peroxide per mole of aminoglycoside to ensure completion of reaction. We usually use a four to five molar excess, although greater molar excesses of hydrogen peroxide are advantageously employed.

Sodium tungstate is usually used as the source of tungstate ion (although other tungstate salts may be used) in catalytic quantities (e.g. 0.05 mole per mole of aminoglycoside).

The oxidation step is usually carried out at room temperature in aqueous methanol, although other lower alkanols, e.g. ethanol and isopropanol, are conveniently employed.

In general, any organic solvent may be used which will dissolve the aminoglycoside and which does not react with hydrogen peroxide, e.g. dimethylacetamide, dimethylformamide, tetrahydrofuran, dioxane and diglyme.

After addition of the tungstate ion, it is necessary that the pH of the reaction mixture be maintained between 9 and 11 (preferably at pH 10 to pH 10.5) such as by addition of a base, e.g. sodium hydroxide, to minimize side reactions occurring such as glycoside cleavage and protonation of the amine.

In the second step of our process, the 2'-oximino-N-protected-4,6-di-O-(aminoglycosyl)-1,3-diaminocyclitol prepared as described above is cleaved to the corresponding 2'-oxo derivative utilizing known techniques for cleaving oximes. We usually cleave the 2'-oximino function by reaction in an acidic hydrolytic medium in the presence of acetaldehyde (e.g. by treating a solution of the 2'-oximino derivative in acetonitrile with 1 N hydrochloric acid containing acetaldehyde) or by reaction of the oximino intermediate with sodium bisulfite followed by mild acid hydrolysis. The latter procedure is usually preferred since greater yields of purer product are usually obtained thereby. When carrying out this procedure, the 2'-oximino-N-protected aminoglycoside intermediate in aqueous ethanol (or other aqueous lower alkanol) is usually reacted with about three to four molar equivalents of sodium bisulfite at reflux temperature until the oximino function is consumed as determined by thin layer chromatographic techniques. There is then added a weak acid (e.g. acetic acid or oxalic or tartaric acid) to produce a mild acid hydrolytic medium; the reaction mixture is then heated at reflux temperature until the reaction is complete as evidenced by thin layer chromatographic techniques and there is produced the corresponding 2'-oxo-N-protected aminoglycoside which can be isolated in good yields via known methods.

Reduction of the 2'-oxo-N-protected aminoglycoside intermediate is preferentially carried out by reaction with an alkali metal borohydride (usually sodium borohydride) according to known procedures for reducing a keto group to a hydroxyl function, and there is obtained an excellent yield of N-protected-2'-hydroxy-2'-desamino-aminoglycoside in which the 2'-hydroxyl function is in the equatorial position, i.e. the same stereoconfiguration as the starting 2'-amino function. After removal of the N-protecting functions according to known techniques, the resulting 2'-hydroxy-2'-desamino-4,6-di-O-(aminoglycosyl)-1,3-diaminocyclitol is isolated and purified utilizing conventional techniques.

When carrying out our process, all the functions desired in the final 2'-hydroxy-2'-desamino derivative of this invention may be present in the 4,6-di-O-(aminoglycosyl)-1,3-diaminocyclitol precursor. Thus, for example, when preparing 1-N-ethyl-2'-hydroxy-2'-desaminosisomicin, or 5-deoxy-2'-hydroxy-2'-desaminosisomicin, the corresponding 1-N-ethylsisomicin or 5-deoxysisomicin may be used as starting compounds. Alternatively, the 2'-amino function in a 4,6-di-O-(aminoglycosyl)-1,3-diaminocyclitol can be replaced by a hydroxyl group via our process, then other functions may be introduced into the 2'-hydroxy-2'-desamino-aminoglycoside by methods known in the art. This alternate method is the method of choice when preparing the preferred 1-N-($\omega$-amino-$\alpha$-hydroxyalkanoyl)-2'-hydroxy-2'-desamino derivatives of this invention. Thus, for example, when preparing 1-N-(S-$\beta$-amino-$\alpha$-hydroxypropionyl)-2'-hydroxy-2'-desaminogentamicin $C_{1a}$ and 1-N-($\gamma$-amino-$\alpha$-hydroxybutyryl)-2'-hydroxy-2'-desaminogentamicin $C_{1a}$, a preferred method involves first converting gentamicin $C_{1a}$ to 2'-hydroxy-2'-desaminogentamicin $C_{1a}$ via the process of this invention, and thence converting 2'-hydroxy-2'-desaminogentamicin $C_{1a}$ to the 1-N-(S-$\beta$-amino-$\alpha$-hydroxypropionyl)- or the 1-N-(S-$\gamma$-amino-$\alpha$-hydroxybutyryl)-2'-hydroxy-2'-desaminogentamicin $C_{1a}$ utilizing techniques known in the art and as described in the examples.

The necessary precursors for our process are 4,6-di-O-(aminoglycosyl)-1,3-diaminocyclitol antibacterial agents having amino functions at the 2',6' and 3"-positions and hydroxyl groups at the 2" and 4"-positions. Included among these are known 4-O-aminoglycosyl-6-O-garosaminyl-2-deoxystreptamine antibiotics such as gentamicin $C_1$, gentamicin $C_{1a}$, gentamicin $C_2$, gentamicin $C_{2a}$, gentamicin $C_{2b}$, sisomicin, verdamicin, Antibiotic JI-20A, Antibiotic JI-20B and Antibiotic G-52; and 4,6-di-O-(aminoglycosyl)-1,3-diaminocyclitols such as tobramycin, Antibiotic 66-40B, Antibiotic 66-40D, Antibiotic Mu-1, Antibiotic Mu-4 and 3',4'-dideoxykanamycin B. Of the foregoing, useful starting antibiotic precursors are sisomicin and gentamicin $C_{1a}$ which lead to preferred 2'-hydroxy-2'-amino derivatives of our invention, and Antibiotic JI-20A which leads to gentamicin B.

Other useful starting antibiotic precursors of our process include 5-epi-4,6-di-O-(aminoglycosyl)-1,3-diaminocyclitol antibacterials described in U.S. Pat. No. 4,000,261; 5-epi-azido-5-deoxy-4,6-di-O-(aminoglycosyl)-1,3-diaminocyclitol antibacterials described in U.S. Pat. No. 4,000,262; 1-N-alkyl-4,6-di-O-(aminoglycosyl)-1,3-diaminocyclitol antibacterials described in U.S. Pat. No. 4,002,742; 5-deoxy-4,6-di-O-(aminoglycosyl)-1,3-diaminocyclitol antibacterials described in copending application Ser. No. 701,387 filed June 30, 1976, now U.S. Pat. No. 4,053,591 and 5-fluoro-5-deoxy-4,6-di-O-(aminoglycosyl)-1,3-diaminocyclitol antibacterials and their 5-epi-fluoro epimers described in copending application Ser. No. 893,638 filed Apr. 4, 1978 as a continuation-in-part of Ser. No. 792,825 filed May 2, 1977, now abandoned, both the foregoing applications being of common assignee as the instant application.

A 2'-hydroxy-2'desamino-4,6-di-O-(aminoglycosyl)-1,3-diaminocyclitol of our invention may be converted to a corresponding 1-N-alkyl derivative or to a corresponding 5-deoxy-, or a 5-epi or 5-epi-azido-5-deoxy derivative, via procedures analogous to those described in the above-mentioned patents and applications.

Thus, for example, a 2'-hydroxy-2'-desamino-4,6-di-O-(aminoglycosyl)-2-deoxystreptamine of this invention (e.g. 2'-hydroxy-2'-desaminosisomicin) is converted to the corresponding 5-deoxy derivative (e.g. 2'-hydroxy-2'-desamino-5-deoxysisomicin) via procedures analogous to those described in U.S. Pat. No. 4,053,591; namely, by first converting said 2'-hydroxy-2'-desamino-4,6-di-O-(aminoglycosyl)-2-dexoystreptamine to the corresponding N- and O-protected (except for the 5-hydroxyl group) intermediate (e.g. 1,3,6'-tri-N-benzyloxycarbonyl-2',2"-di-O-benzoyl-3",4"-N,O-carbonyl-2'-hydroxy-2'-desaminosisomicin) utilizing known techniques, then converting the 5-hydroxyl group to the 5-O-thioformate ester by reaction with the Vilsmaier salt produced from phosgene and N,N-dimethylformamide in dichloromethane, followed by reaction of the imidinium chloride salt thereby produced (e.g. 1,3,6'-tri-N-benzyloxycarbonyl-2',2''-di-O-benzoyl-3'',4''-N,O-carbonyl-2'-hydroxy-2'-desaminosisomicin-5-O-(N,N-dimethylformimidinium)chloride) with hydrogen sulfide in pyridine, thence reaction of the requisite 5-O-thioformyl ester thereby formed (e.g. 1,3,6'-tri-N-benzyloxycarbonyl-5-O-thioformyl-2',2''-di-O-benzoyl-3'',4''-N-O-carbonyl-2'-hydroxy-2'-desaminosisomicin) with tri-n-butylstannane in toluene and, finally, removal of the N- and O-protecting groups in the resulting 5-deoxy derivative via known procedures to obtain a 5-deoxy-2'-desamino-2'-hydroxy compounds of this invention (e.g. 2'-hydroxy-2'-desamino-5-deoxysisomicin).

Similarly, a 2'-hydroxy-2'-desamino-4,6-di-O-(aminoglycosyl)-2-dexoystreptamine of this invention is converted to the corresponding 5-epi-fluoro-5-deoxy derivative according to procedures analogous to those described in U.S. Ser. No. 893,638 filed Apr. 4, 1978 whereby an N- and O-protected-2'-hydroxy-2'-desamino-4,6-di-O-(aminoglycosyl)-2-deoxystreptamine having a free 5-hydroxyl group (e.g., 1,3,6'-tri-N-benzyloxycarbonyl-2',2''-di-O-benzoyl-3'',4''-N,O-carbonyl-2'-hydroxy-2'-desaminosisomicin) is reacted with a dialkylaminosulfur trifluoride, preferably diethylaminosulfur trifluoride in methylene chloride, followed by treatment with sodium bicarbonate and then removal of the N- and O-protecting groups to obtain a 5-epi-fluoro-2'-hydroxy-2'-desamino-4,6-di-O-(aminoglycosyl)-2,5-dideoxystreptamine of this invention (e.g. 5-epi-fluoro-2'-hydroxy-2'-desamino-5-deoxysisomicin).

The requisite N-protected starting intermediates of our process are 4,6-di-O-(aminoglycosyl)-1,3-diaminocyclitols wherein all amino functions except the 2'-amino group therein are protected by amino protecting groups, preferably by acyl groups which together with the amine being protected form amide functions susceptible to reductive cleavage or basic hydrolysis.

In this specification and in the claims, by "acyl" is meant an organic radical derived from any organic acid by removal of the hydroxyl group.

The term "amino protecting group" is well known in the art and refers to a large number of groups suitable for temporarily protecting an amino function in a molecule from undergoing chemical reactions, yet are readily removed after a desired chemical reaction has taken place. The amino protecting groups defined by "Y" hereinabove are preferably acyl functions including hydrocarbonyloxycarbonyl groups such as benzyloxycarbonyl, substituted benzyloxycarbonyl (including o, m and p-methoxybenzyloxycarbonyl), alkoxycarbonyl (e.g., methoxycarbonyl, ethoxycarbonyl, n-butoxycarbonyl, tert.-butoxycarbonyl, octyloxycarbonyl, trichlorethoxycarbonyl) as well as hydrocarboncarbonyl groups such as acetyl, propionyl, and benzoyl. The choice of protecting group depends on the amino groups being protected, subsequent reaction conditions, and conditions for removal. This choice is within the ability of those skilled in the art.

The preferred acyl protecting groups of this invention are conveniently prepared by combining procedures known in the art, together with a selective blocking procedure described in copending application Ser. No. 697,297, filed June 17, 1976 of T. L. Nagabhushan et al, of common assignee as the instant application. By the selective blocking procedure, a transition metal salt complex between available neighboring amino and hydroxyl functions in said 4,6-di-O-(aminoglycosyl)-1,3-diaminocyclitol and cupric acetate or nickel (II) acetate is first prepared followed by introduction of acyl functions on non-complexed and/or weakly complexed amino functions, and thence removal of said transition metal salt complex by means of hydrogen sulfide or ammonium hydroxide.

When preparing N-protected starting intermediates of saturated aminoglycosides having a primary carbinamine at C-5', e.g. a 1,3,6',3''-tetra-N-protected gentamicin $C_{1a}$, we usually prefer to block the amino functions by hydrocarbonyloxycarbonyl groups which are susceptible to reductive cleavage (e.g. with sodium in ammonia) or to alkaline hydrolysis, e.g. by utilizing blocking groups such as benzyloxycarbonyl, ethoxycarbonyl, and methoxycarbonyl groups. Such an N-protected intermediate, e.g. 1,3,6',3''-tetra-N-benzyloxycarbonyl-gentamicin $C_{1a}$, is conveniently prepared by first reacting the unblocked aminoglycoside, e.g. gentamicin $C_{1a}$, with about two equivalents of N-(trichloroethoxycarbonyloxy)succinimide in methanol in the presence of excess nickel acetate according to the selective blocking procedure whereby, after decomposition of the nickel acetate complex by means of ammonium hydroxide, there is produced 2',6'-di-N-trichloroethoxycarbonyl-gentamicin $C_{1a}$; secondly, preparing the N-benzyloxycarbonyl derivatives of the remaining amino functions at the 1,3 and 3''-positions via the well known procedure utilizing benzylchloroformate and calcium hydroxide; third, treating the resulting 1,3,3''-tri-N-benzyloxycarbonyl-2',6'-di-N-(trichloroethoxycarbonyl)-gentamicin $C_{1a}$ with zinc in acetic acid whereby are removed the trichloroethoxycarbonyl groups to produce 1,3,3''-tri-N-benzyloxycarbonylgentamicin $C_{1a}$; thence, finally, blocking the more reactive 5'-primary carbinamine group by reaction of the 1,3,3''-tri-N-blocked derivative with about one equivalent of N-(benzyloxycarbonyloxy)phthalimide in the presence of excess triethylamine to produce the desired 1,3,6',3''-tetra-N-benzyloxycarbonylgentamicin $C_{1a}$, a requisite intermediate of the process of this invention.

When preparing N-blocked aminoglycoside intermediates of saturated 4,6-di-O-(aminoglycosyl)-1,3-diaminocyclitols having a secondary amino function at the 6'-position (such as in gentamicin $C_1$) the requisite 1,3,6',3''-tetra-N-blocked intermediate (e.g., 1,3,6',3''-tetra-N-ethoxycarbonylgentamicin $C_1$) may be prepared by first reacting gentamicin $C_1$ with about one equivalent of N-benzyloxycarbonyloxysuccinimide in the presence of about three equivalents of cupric acetate according to the selective blocking procedure whereby, after decomposition of the copper complex with ammonium hydroxide, there is obtained 2'-N-benzyloxycarbonylgentamicin $C_1$. Reaction of the foregoing derivative with over four equivalents of ethoxycarbonyl chloride and sodium carbonate, followed by removal of the 2'-benzyloxycarbonyl group via reductive cleavage by means of hydrogen in the presence of palladium-on-charcoal catalyst yields 1,3,6',3''-tetra-N-ethoxycarbonylgentamicin $C_1$, a requisite intermediate of this invention.

When preparing 2'-hydroxy-2'-desamino-4,6-di-O-(aminoglycosyl)-1,3-diaminocyclitols having double bonds, such as in sisomicin, the N-blocking groups in the unsaturated aminocyclitol are preferably N-benzoyl blocking groups since such derivatives are less susceptible to glycoside cleavage under the acidic reaction conditions necessary for the deoximation step of our process. Thus, a preferred N-blocked sisomicin starting intermediate is 1,3,6'-tri-N-benzoyl-3''-N-acetylsisomicin, which is conveniently prepared by first treating sisomicin with excess N-benzoyl imidazole followed by treatment of the resulting 6'-N-benzoylsisomicin with one equivalent of N-(trichloroethoxycarbonyloxy)succinimide in methanol in the presence of nickel (II) acetate according to the selective blocking procedure whereby (after decomposition of the nickel acetate complex by means of ammonium hydroxide) is produced mainly 2'-trichloroethoxycarbonyl-6'-N-benzoylsisomicin. Treatment of the foregoing with excess benzoic anhydride in methanol yields 1,3,6'-tri-N-benzoyl-2'-(trichloroethoxycarbonyloxy)sisomicin which, upon reaction with excess acetic anhydride followed by treatment with zinc in acetic acid in methanol yields 1,3,6'-tri-N-benzoyl-3''-N-acetylsisomicin, a requisite intermediate of this invention.

When preparing N-protected starting intermediates of aminoglycosides having amino groups at the 2' and 6'-positions and hydroxyl groups at the 3' and 4'-positions (e.g. a 1,3,6',3''-tetra-N-protected-Antibiotic JI-20A), we prefer to first protect the 6'-position by reacting the aminoglycoside with about one equivalent of N-benzyloxycarbonyloxyphthalimide in the presence of about one equivalent of cupric chloride according to the selective blocking procedure whereby, after decomposition of the copper complex with ammonium hydroxide there is obtained the 6'-N-benzyloxycarbonyl derivative (e.g. 6'-N-benzyloxycarbonyl-Antibiotic JI-20A). We then protect the 2'-position by reaction of the foregoing 6'-N-substituted derivative with about a mole of either N-tert.-butoxycarbonyloxyphthalimide or N-(2,2,2-trichloroethoxy)carbonyloxyphthalimide in the presence of about an equivalent of nickel acetate according to the selective blocking method whereby, after decomposition of the nickel complex with ammonium hydroxide, the corresponding 2'-N-tert.-butoxycarbonyl or 2'-N-(2,2,2-trichloroethoxycarbonyl) derivative is formed (e.g. 2'-N-tert.-butoxycarbonyl- or 2'-N-(2,2,2-trichloroethoxycarbonyl)-6'-N-benzyloxycarbonyl-Antibiotic JI-20A). Reaction of the foregoing 2',6'-di-N-protected aminoglycoside with over three equivalents of benzyloxycarbonylchloride according to standard blocking procedures followed by removal of the 2'-N-tert.-butoxycarbonyl-protecting group with trifluoroacetic acid or removal of the 2'-N-(2,2,2-trichloroethoxy)-protecting group by treatment with trifluoroacetic acid or zinc and acetic acid in methanol respectively yields a 1,3,6',3''-tetra-N-protected-Aminoglycoside starting compound of this invention, e.g. 1,3,6',3''-tetra-N-benzyloxy-Antibiotic JI-20A.

It will be obvious to one skilled in the art that other requisite 1,3,6',3''-tetra-N-acyl aminoglycoside starting compounds of this process can be prepared by other combinations of acylating procedures known in the art together with the selective blocking procedures disclosed in co-pending application Ser. No. 697,897 filed June 17, 1976.

PREPARATION 1

1,3,6',3''-Tetra-N-Benzyloxycarbonylgentamicin $C_{1a}$

A.

2',6'-Di-N-(2,2,2-Trichloroethoxycarbonyl)Gentamicin $C_{1a}$

To a solution of gentamicin $C_{1a}$ (5.0 gms.) and nickel (II) acetate (10.0 gms.) in methanol (250 ml.) at 0° C. with stirring add N-(2,2,2-trichloroethoxycarbonyloxy)succinimide (6.25 gms.). Allow the solution to reach room temperature and stir at room temperature for an hour, then evaporate in vacuo until the reaction solution has a volume of about 100 ml. Add 2 N ammonium hydroxide (500 ml.), extract with chloroform (three 120 ml. portions), dry the combined extracts with potassium carbonate and evaporate. Purify the resultant residue by chromatography on silica gel (300 gms.) eluting with a chloroform:methanol:concentrated ammonium hydroxide (4:1:0.1) solvent system. Combine the like eluates of desired product as determined by thin layer chromatography and evaporate. Dissolve the resultant residue in chloroform (30 ml.), add the chloroform solution to a stirred mixture of hexane (400 ml.) and ether (100 ml.). Separate the resultant precipitate by filtration and dry at 60° C. in vacuo (1 mm.) to obtain 2',6'-di-N-(2,2,2-trichloroethoxycarbonyl)gentamicin $C_{1a}$; yield 4.9 gms.; 62% theory; m.p. 119°–122° C.; $[\alpha]_D^{26}$ +95.4° (chloroform, c=0.48).

B. 1,3,3''-Tri-N-Benzyloxycarbonylgentamicin $C_{1a}$

To a solution of 2,6'-di-N-(2,2,2-trichloroethoxycarbonyl)gentamicin $C_{1a}$ (17.0 gms.) and calcium hydroxide (25 gms.) in methanol (250 ml.) cooled to 5° C., add over a 2-minute interval benzoyl chloroformate (25 ml.). Allow the solution to reach room temperature and stir at room temperature for 30 minutes. Dilute the reaction mixture (now containing 1,3,3''-tri-N-benzyloxycarbonyl-2',6-di-N-(2,2,2-trichloroethoxycarbonyl)gentamicin $C_{1a}$) with methanol (250 ml.), water (100 ml.) and acetic acid (75 ml.). Add zinc dust (40 gms.) and stir at room temperature for 30 minutes, then stir and heat at reflux temperature for one hour. Cool, remove the zinc by filtration and wash with methanol (two portions of 25 ml.). Add the combined filtrate and washings to a mixture of ice (1000 gms.) and concentrated ammonium hydroxide (500 ml.). Extract the aqueous mixture with chloroform (800 ml.), then two 300 ml. portions. Wash the combined extracts with water and evaporate. Chromatograph the resultant residue on silica gel (350 gms.) eluting with a solvent mixture of chloroform:methanol:concentrated ammonium hydroxide (10:1:0.1). Evaporate the combined, like eluates as determined by thin layer chromatography dissolve the resultant residue in chloroform (50 ml.), and add the chloroform solution dropwise to a stirred mixture of ether (100 ml.) and hexane (700 ml.). Separate the resultant precipitate by filtration and dry in vacuo at 60° C. to give 1,3,3''-tri-N-benzyloxycarbonylgentamicin $C_{1a}$; yield 11.7 gms.; 65% theory; m.p. 110°–113° C.; $[\alpha]_D^{26}$ 96.5° (chloroform, c=0.55).

C. 1,3,6',3''-Tetra-N-Benzyloxycarbonylgentamicin $C_{1a}$

To a stirred solution of 1,3,3''-tri-N-benzyloxycarbonylgentamicin $C_{1a}$ (9.35 gms.) and triethylamine (6.0 ml.) in chloroform (100 ml.) at 0°–5° C., add dropwise over a 5-minute period a solution of N-(benzyloxycarbonyloxy)phthalimide (3.2 gms.) in chloroform (90 ml.). Stir the reaction mixture an additional 10 minutes, then wash the reaction mixture with ammonium hydroxide (2 Normal). Dry over potassium carbonate and evaporate. Chromatograph the resultant residue on silica gel (200 gms.) eluting with a solvent mixture comprising chloroform:methanol:concentrated ammonium hydroxide (20:1:0.1). Combine the like eluates containing the desired product as determined by thin layer chromatography and evaporate. Dissolve the resultant residue in a minimum quantity of chloroform and add the chloroform dropwise to hexane (500 ml.). Separate the resultant precipitate by filtration, dry in vacuo at 60° C. to give 1,3,6',3''-tetra-N-benzyloxycarbonylgentamicin $C_{1a}$; yield 8.5 gms. (79% theory); m.p. 101°–104° C.; $[\alpha]_D^{26}$ +73.9° (chloroform, c=0.48).

PREPARATION 2

3''-N-Acetyl-1,3,6'-Tri-N-Benzoylsisomicin

A. 6'-N-Benzoylsisomicin

To a solution of sisomicin (10 gms.) in methanol (100 ml.) at 0°–5° C., add dropwise a solution of N-benzoyl imidazole (7 gms., 2 equivalents) in chloroform (30 ml.). Stir the reaction mixture at room temperature for 30 minutes, concentrate in vacuo to a small volume, dissolve the resultant syrupy residue in chloroform (70 ml.) and add the chloroform solution slowly to stirred ether (650 ml.). Separate the resultant precipitate by filtration, wash with ether and dry in vacuo at 50° C. to obtain 6'-N-benzoylsisomicin (14 gms.) which is used without further purification in the procedure of Preparation 2B.

B.
2'-N-(2,2,2-Trichloroethoxycarbonyl)-6'-N-Benzoylsisomicin

Dissolve 6'-N-benzoylsisomicin (14 gms.) in methanol (450 ml.) and add nickel (II) acetate (25 gms.) and stir for 20 minutes at room temperature. Cool the reaction mixture to 0°–5° C., and add dropwise a solution of N-(2,2,2-trichloroethoxycarbonyloxy)succinimide (6.4 gms., 1.1 equivalents) in chloroform (40 ml.). Stir at room temperature for 30 minutes, then add concentrated ammonium hydroxide (25 ml.) and evaporate in vacuo to a volume of about 100 ml. Dilute the resultant residue with 3 N ammonium hydroxide (250 ml.) and extract with chloroform (two 200 ml. portions). Dry the combined extracts over potassium carbonate, filter and evaporate in vacuo to a residue comprising 2'-N-(2,2,2-trichloroethoxycarbonyl)-6'-N-benzoylsisomicin, which is used without further purification in the procedure of Preparation 2C.

C.
1,3,6'-Tri-N-Benzoyl-2'-N-(2,2,2-trichloroethoxycarbonyl)Sisomicin

Prepare a solution of 2'-N-(2,2,2-trichloroethoxycarbonyl)-6'-N-benzoylsisomicin product of Preparation 2B in methanol (120 ml.), and chloroform (60 ml.), then with stirring add anhydrous sodium carbonate (20 gms.) followed by a dropwise addition of benzoic anhydride (12.1 gms.) in chloroform (40 ml.). Stir the reaction mixture at room temperature for one hour, add chloroform (300 ml.) and wash the organic solution with water (150 ml.). Evaporate the organic phase in vacuo to a volume of about 100 ml., then to the resulting suspension add ether (500 ml.) with agitation. Separate the resultant precipitate by filtration and wash with ether to obtain 1,3,6'-tri-N-benzoyl-2'-N-(2,2,2-trichloroethoxycarbonyl)sisomicin, which is used without further purification in the procedure of Preparation 2D.

D. 1,3,6'-Tri-N-Benzoylsisomicin

To a solution of 1,3,6'-tri-N-benzoyl-2'-N-(2,2,2-trichloroethoxycarbonyl)sisomicin product of Preparation 2C in methanol (250 ml.) and acetic acid (30 ml.), add with stirring zinc dust (30 gms.) and stir for 30 minutes a room temperature and at reflux temperature for 1½ hours. Decant the reaction solution (from any undissolved zinc which may remain) into 2 N ammonium hydroxide (1.2 liters) and extract the aqueous mixture with chloroform (three 500 ml. portions). Dry the combined extracts over potassium carbonate, filter and evaporate in vacuo. Dissolve the resultant residue in hot methanol (50 ml.), add warm ethyl acetate (250 ml.) and stir the mixture gently for 18 hours at room temperature. Separate the resultant precipitate by filtration, wash with ethyl acetate and dry in vacuo at 60° C. to obtain 1,3,6'-tri-N-benzoylsisomicin; yield 7.0 gms.; m.p. 233°–236° C.; $[\alpha]_D^{26}$ +97.4° (aqueous tetrahydrofuran, c=0.50).

E. 1,3,6'-Tri-N-Benzoyl-3''-N-Acetylsisomicin

To a solution of 1,3,6'-tri-N-benzoylsisomicin (16.0 gms.) in tetrahydrofuran (300 ml.) and water (200 ml.) add with stirring over a 15-minute interval a solution of N-(2,2,2-trichloroethoxycarbonyloxy)succinimide (6.1 gms.) in tetrahydrofuran (70 ml.). Stir the reaction mixture for 15 minutes, then add acetic anhydride (20 ml.) and continue stirring the reaction mixture for one hour at room temperature. Add 500 ml. of chloroform, then with stirring add sodium carbonate (30 gms.). Separate the organic and aqueous phases, evaporate the organic phase in vacuo, dissolve the resultant residue in methanol (165 ml.) and acetic acid (15 ml.). Add zinc dust (20 gms.), stir for 30 minutes, then add additional acetic acid (5 ml.). Stir the reaction mixture at reflux temperature for 1 hour, then cool and decant from any excess zinc into a mixture of ice (400 gms.) and concentrated ammonium hydroxide (200 ml.). Extract the mixture with chloroform (three portions) of 300 ml.). Dry the combined extracts over potassium carbonate and evaporate in vacuo. Chromatograph the resultant residue on silica gel (about 300 gms.) eluting with a solvent mixture comprising chloroform:methanol:concentrated ammonium hydroxide (10:1:0.1). Evaporate the combined, like fractions containing the desired product as determined by thin layer chromatography, dissolve the resultant residue in chloroform (50 ml.) and methanol (5 ml.) and add to a stirred mixture of ether (700 ml.) and hexane (350 ml.). Collect the resultant precipitate by filtration, wash with ether, and dry in vacuo at 60° C. to obtain 1,3,6'-tri-N-benzoyl-3''-N-acetylsisomicin; yield 9.3 gms.; m.p. ca 220° C. (decomp.); $[\alpha]_D^{26}$ +121° (dimethylformamide, c=0.40).

PREPARATION 3

1,3,6',3''-Tetra-N-Ethoxycarbonylgentamicin $C_1$

A. 2'-N-Benzyloxycarbonylgentamicin $C_1$

To a stirred solution of gentamicin $C_1$ (30 gms.) in dimethylsulfoxide (5.4 liters) add cupric acetate monohydrate (37.2 gms.). Stir until solution occurs, then add N-benzyloxycarbonyloxysuccinimide (22.2 gms.) in tetrahydrofuran (100 ml.). Stir the reaction mixture for 30 minutes, pour into water (3 liters) extract continuously with chloroform and discard the chloroform extracts. To the aqueous solution add acetyl acetone (20 ml.), stir vigorously at room temperature for 3 hours, then filter. Pass the filtrate through IRA-401S (OH$^-$) resin (300 mg.), then freeze-dry and chromatograph the resultant residue over silica gel (500 gms.) eluting with a solvent mixture comprising chloroform:methanol:15% ammonium hydroxide (2:1:1). Evaporate the combined, like eluates containing the desired product as determined by thin layer chromatography to a residue of 2'-N-benzyloxycarbonylgentamicin $C_1$; yield 7.3 gms.

B.
1,3,6',3''-Tetra-N-Ethoxycarbonyl-2'-N-Benzyloxycarbonylgentamicin $C_1$

To a solution of 2'-N-benzyloxycarbonylgentamicin $C_1$ (5.7 gms.) and sodium carbonate (19.6 gms.) in methanol (200 ml.) and water (200 ml.) at 0°–4° C., add with stirring ethoxycarbonyl chloride (6.72 ml.) and vigorously stir the reaction mixture for 24 hours at 0°–4° C. Separate the resultant precipitate by filtration, wash with water (two portions of 100 ml.), dry in vacuo at 45° C. to a residue comprising 1,3,6',3''-tetra-N-ethoxycarbonyl-2'-benzyloxycarbonylgentamicin $C_1$. Additional product is obtained by extracting the filtrate with chloroform, drying the chloroform extracts over magnesium sulfate and evaporating the combined extracts in vacuo. Combine both the foregoing residues and purify by passing through silica gel (36 gms.) eluting with chloroform:methanol (98:2). Evaporate the combined eluates to obtain 1,3,6',3''-tetra-N-ethoxycarbonyl-2'-N-benzyloxycarbonylgentamicin $C_1$; yield 6.89 gms.

C. 1,3,6',3''-Tetra-N-Ethoxycarbonylgentamicin $C_1$

Dissolve the 1,3,6',3''-tetra-N-ethoxycarbonyl-2'-N-benzyloxycarbonylgentamicin $C_1$ (6.89 gms.) product of Preparation 3B in ethanol (200 ml.) and hydrogenate utilizing 30% palladium-on-charcoal catalyst (30%, 0.5 gms.) Filter the reaction mixture, evaporate the filtrate and chromatograph the resultant residue over silica gel (25 gms.) eluting with chloroform:methanol (95:5). Evaporate the combined, like eluates to a residue comprising 1,3,6',3''-tetra-N-ethoxycarbonylgentamicin $C_1$, yield 5.1 gms.

PREPARATION 4

1,3,6',3''-Tetra-N-Ethoxycarbonylgentamicin $C_{2b}$

Subject gentamicin $C_{2b}$ to the series of reactions described in Preparations 3A, 3B and 3C to obtain 1,3,6',3''-tetra-N-ethoxycarbonylgentamicin $C_{2b}$.

PREPARATION 5

1,3,6'-Tri-N-benzoyl-3''-N-acetyl-4'(5')-dehydro aminoglycosides

Subject each of the following aminoglycosides to the series of reactions described in Preparation 2(A)–(E): Antibiotic G-52, Antibiotic 66-40D, Antibiotic 66-40B, verdamicin, Antibiotic Mu-1, 5-deoxysisomicin, Antibiotic Mu-4, 5-episisomicin, 5-epi-azido-5-deoxysisomicin, and 1-N-ethylsisomicin. Isolate and purify each of the resultant products in a manner similar to that described in Preparation 2E to obtain the 1,3,6'-tri-N-benzoyl-3''-N-acetyl derivative of each of the aforenamed starting aminoglycosides.

PREPARATION 6

1,3,6',3''-Tetra-N-benzyloxycarbonyl derivatives of tobramycin, gentamicin $C_2$, and gentamicin $C_{2a}$ A. 1,3,6',3''-Tetra-N-Benzyloxycarbonyltobramycin, Gentamicin $C_2$, and Gentamicin $C_{2a}$ Subject each of tobramycin, gentamicin $C_2$, gentamicin $C_{2a}$ and 3',4'-dideoxykanamycin B to the series of reactions described in Preparations 1A, 1B, 1C and isolate each of the resultant products in a manner similar to that described to obtain, respectively, 1,3,6',3''-tetra-N-benzyloxycarbonyltobramycin, 1,3,6',3''-tetra-N-benzyloxycarbonylgentamicin $C_2$, 1,3,6',3''-tetra-N-benzyloxycarbonylgentamicin $C_{2a}$ and 1,3,6',3''-tetra-N-benzyloxycarbonyl-3',4'-dideoxykanamycin B.

PREPARATION 7

1,3,6',3''-Tetra-N-Benzyloxycarbonyl derivatives of antibiotics JI-20A and JI-20B A. 6'-N-Benzyloxycarbonyl-Antibiotic JI-20A To a solution of Antibiotic JI-20A (1.44 gms.) in water (1.5 ml.), dimethylsulfoxide (58.5 ml.) and triethylamine (0.6 ml.) add cupric chloride (0.51 gms.). Stir for 15 minutes at room temperature, then add N-benzyloxycarbonyloxyphthalimide (0.910 gms.) and dissolve in dimethylsulfoxide (5 ml.). After 1 hour add additional N-benzyloxycarbonyloxyphthalimide (0.6 gms.) in dimethylsulfoxide (4 ml.) and stir. Pour the reaction mixture into ether, decant, add ether and stir, then decant again and repeat this procedure several times. Dissolve the resulting syrupy residue in 200 ml. of methanol, bubble hydrogen sulfide through the methanol solution, separate the resulting copper sulfide salt precipitate by filtration, stir the filtrate with IRA-401S (OH$^\ominus$) resin (50 ml.) and separate the resin by filtration. Evaporate the filtrate and chromatograph the resultant residue on silica gel (100 gms.) eluting with chloroform:methanol:28% ammonium hydroxide (2:1:0.35). Combine the like fractions containing the desired product as determined by thin layer chromatography and evaporate to a residue comprising 6'N-benzyloxycarbonyl-Antibiotic JI-20A.

B.
2'-N-Tert.-Butoxycarbonyl-6'-N-Benzyloxycarbonyl-Antibiotic JI-20A

Dissolve 6'-N-benzyloxycarbonyl-Antibiotic JI-20A (0.517 gms.) in methanol (15 ml.), then add nickel (II) acetate tetrahydrate (0.21 gms.) and stir at room temperature for 15 minutes. Add N-tert.-butoxycarbonyloxyphthalimide (0.22 gms.) and stir for 3 hours while adding every hour additional portions of N-tert.-butoxycarbonyloxyphthalimide (0.2 gms. each). Bubble hydrogen sulfide through the reaction mixture, separate the resultant nickel salts by filtration, stir the filtrate with IRA-401S (OH$^\ominus$) resin (20 ml.) and separate the resin by filtration. Evaporate the filtrate and chromatograph the resultant syrupy residue on 50 gms. of silica gel eluting with chloroform:methanol:28% ammonium hydroxide (30:10:1). Combine the like fractions containing the desired products as determined by thin layer chromatography and evaporate to a residue comprising 2'-N-tert.-butoxycarbonyl-6'-N-benzyloxycarbonyl-Antibiotic JI-20A.

C.
1,3,6',3''-Tetra-N-Benzyloxycarbonyl-2'-N-Tert.-Butoxycarbonyl-Antibiotic JI-20A Dissolve 2'-N-tert.-butoxycarbonyl-6'-N-benzyloxycarbonyl-Antibiotic JI-20A (0.716 gms.) in methanol (15 ml.) and stir (5 ml.). Cool the solution to 0° C., add sodium carbonate (0.53 gms.) and then add benzyloxycarbonyl chloride (0.74 ml.). Allow the reaction mixture to stand for 3 hours, then pour into 50 ml. of water. Separate the resultant precipitate by filtration, wash the precipitate with water and then ether, then dry in vacuo to obtain 1,3,6',3''-tetra-N-benzyloxycarbonyl-2'-N-tert.-butoxycarbonyl-Antibiotic JI-20A.

D. Dissolve 1,3,6',3''-tetra-N-benzyloxycarbonyl-2'-N-tert.-butoxycarbonyl-Antibiotic JI-20A (1.121 gms.) in trifluoroacetic acid (5 ml.). Allow the reaction mixture to stand at room temperature for 3 minutes, then add 50 ml. of ether and separate the resultant precipitate by filtration. Dissolve the precipitate in methanol (30 ml.) and stir with IRA-101S (OH$^\ominus$) ion exchange resin (10 ml.). Separate the resin by filtration, add ether to the filtrate and separate the resultant precipitate by filtration to obtain 1,3,6',3''-tetra-N-benzyloxycarbonyl-Antibiotic JI-20A.

E. 1,3,6',3''-Tetra-N-Benzyloxycarbonyl-Antibiotic JI-20B

Treat Antibiotic JI-20B in a manner similar to that described in above Preparations 7A, 7B, 7C and 7D to obtain 1,3,6',3''-tetra-N-benzyloxycarbonyl-Antibiotic JI-20B.

EXAMPLE 1

2'-HYDROXY-2'-DESAMINOGENTAMICIN $C_{1a}$
(3',4'-DIDEOXYGENTAMICIN B)

A.
1,3,6',3''-Tetra-N-Benzyloxycarbonyl-2'-Oximino-2'-Desamino-Gentamicin $C_{1a}$ Stir a solution of 1,3,6',3''-tetra-N-benzyloxycarbonylgentamicin $C_{1a}$ (7.0 gms.) in methanol (80 ml.) with aqueous hydrogen peroxide (30%, 5 gms.), then add a solution of sodium tungstate (0.3 gms.) in water (2 ml.). Stir the reaction mixture at 15°–20° C. keeping the solution at a pH of about 10–10.5 by periodic small additions of 1 N sodium hydroxide. Monitor the progress of the reaction via thin layer chromatography for almost complete consumption of the 2'-amino function (4–5 hours). Add the reaction mixture to water (700 ml.) containing concentrated hydrochloric acid (2 ml.). Extract the aqueous mixture with chloroform (two portions of 250 ml.), wash the combined extracts with water, dry over magnesium sulfate and evaporate. Purify the resultant residue via rapid chromatography on silica gel (200 gms.) eluting with 4% chloroform in methanol. Combine the like eluates containing the mixture of syn and anti of the desired 2'-oximino product and evaporate in vacuo at 60° C. to obtain an isomeric mixture of syn and anti 1,3,6',3''-tetra-N-benzyloxycarbonyl-2'-oximino-2'-desaminogentamicin $C_{1a}$; yield 5.70 gms.; 80% theory, which is used without further purification in the procedure of following Example 1B.

B.
1,3,6',3''-Tetra-N-Benzyloxycarbonyl-2'-Oxo-2'-Desamino-Gentamicin $C_{1a}$

Stir at reflux temperature a solution of 1,3,6',3''-tetra-N-benzyloxycarbonyl-2'-oximino-2'-desaminogentamicin $C_{1a}$ (isomeric mixture prepared as described in Example 1A) and sodium bisulfite (5.5 gms.) in ethanol (65 ml.) and water (28 ml.). After stirring for 10 minutes, add additional sodium bisulfite (2.5 gms.) and continue stirring at reflux temperature for 45 minutes. Add acetic acid (15 ml.), stir the reaction mixture at reflux temperature an additional 45 minutes, then pour into water (500 ml.). Extract the aqueous mixture with chloroform, wash the combined chloroform extracts with aqueous sodium bicarbonate solution, dry the chloroform over sodium sulfate and evaporate to a residue comprising 1,3,6',3''-tetra-N-benzyloxycarbonyl-2'-oxo-2'-desaminogentamicin $C_{1a}$ which is used without further purification in the procedure of following Example 1C.

C.
1,3,6',3''-Tetra-N-Benzyloxycarbonyl-2'-Hydroxy-2'-Desamino-Gentamicin $C_{1a}$ Dissolve the 1,3,6',3''-tetra-N-benzyloxycarbonyl-2'-oxo-2'-desaminogentamicin $C_{1a}$ prepared in Example 1B in tetrahydrofuran (35 ml.) and ethanol (35 ml.), and with stirring add a solution of sodium borohydride (1 gm.) in water (5 ml.). Stir the reaction mixture at room temperature for 10 minutes, then carefully add acetic acid until the solution is at a pH of about 10. Pour the reaction mixture into a large volume of water and extract with chloroform. Wash the combined chloroform extracts with water, dry over magnesium sulfate and evaporate in vacuo and dry the resultant residue at 60° C. in vacuo to obtain 1,3,6',3''-tetra-N-benzyloxycarbonyl-2'-hydroxy-2'-desaminogentamicin $C_{1a}$ which is used without further purification in the procedure of following Example 1D.

D. Dissolve the 1,3,6',3''-tetra-N-benzyloxycarbonyl-2'-hydroxy-2'-desaminogentamicin $C_{1a}$ prepared in Example 1C in dry tetrahydrofuran (12 ml.) and add this solution dropwise to a stirred solution of sodium (1.5 gms.) in liquid ammonia (70 ml.). Stir the reaction mixture for 10 minutes, then add methanol (20 ml.) and water (100 ml.) and evaporate in vacuo to a volume of about 75 ml. Pour onto excess IRC-50 (H$^\oplus$) resin, wash the resin with water, then elute with 1 N ammonium hydroxide. Evaporate the combined, like eluates containing the desired product as determined by thin layer chromatography, evaporate, and chromatograph the resultant residue on silica gel (50 gms.) eluting with solvent mixture comprising chloroform:methanol:concentrated ammonium hydroxide (2:1:0.2). Again evaporate the combined eluates containing the desired product as determined by thin layer chromatography, dissolve the resultant residue in water and pass through IRA-401 (OH$^\ominus$) resin. Lyophilize the combined eluates to a residue of 2'-hydroxy-2'-desaminogentamicin $C_{1a}$; yield 971 mg., 67% theory; m.p. 110°–114° C; $[\alpha]_D^{26}$ +162.4° (water, c=0.33). Combustion analysis: Found: C, 49.2; H, 8.5; N, 11.8. $C_{19}H_{38}N_4O_8 \cdot H_2O$ req. C, 49.7; H, 8.6; N, 12.0%. pmr spectrum in deuterium oxide: 1.16 (s, 3,4''—CCH$_3$), 2.47 (s, 3,3''—NCH$_3$), 3.75 (dd, $J_1''2''=4$ Hz, $J_2''3''=10.5$ Hz, 1, $H_2''$), 4.00 (d, $J_5''ax-5''eq=12.5$ Hz, 1, $H_5''eq$), 5.04 (d, $H_1''2''=4$ Hz, 1, $H_1''$) and 5.18 (d, $H_1'2'=3.5$ Hz, 1, $H_1'$).

EXAMPLE 2

1-N-(AMINOHYDROXYALKANOYL)-2'-HYDROXY-2'-DESAMINOGENTAMICIN $C_{1a}$

A.

3',6'-Di-N-Benzyloxycarbonyl-2'-Hydroxy-2'-Desamino-Gentamicin $C_{1a}$

Stir a solution of 2'-hydroxy-2'-desaminogentamicin $C_{1a}$ (710 mg.) in dimethylsulfoxide (28 ml.) at room temperature, then add powdered cupric acetate (600 mg.) and nickelous acetate (750 mg.). Continue stirring for 30 minutes, then add dropwise a solution of N-(benzyloxycarbonyloxy)phthalimide (1.05 gms.) in dry dimethylsulfoxide (6 ml.) and continue stirring for 15 minutes. Add the reaction solution to aqueous ammonium hydroxide (2 N; 250 ml.) and extract with chloroform (three 150 ml. portions). Wash the combined organic extracts with water (50 ml.), dry over potassium carbonate, filter and evaporate to a residue comprising 3,6'-di-N-benzyloxycarbonyl-2'-hydroxy-2'-desaminogentamicin $C_{1a}$, which is used without further purification in aqueous methanol in the procedure of Example 2B(1).

B.

3,6'-Di-N-Benzyloxycarbonyl-1-N-[S-γ-(benzyloxycarbonylamino)-α-Hydroxybutyryl]-2'-hydroxy-2'-desaminogentamicin $C_{1a}$ (1) The requisite active ester reagent N-[S-γ-benzyloxycarbonylamino)-α-hydroxybutyryloxy]succinimide in tetrahydrofuran is prepared as follows. To a stirred solution of S-γ-(benzyloxycarbonylamino)-α-hydroxybutyric acid (0.60 gms.) and dry N-hydroxysuccinimide (0.38 gms.) in dichloromethane (10 ml.) and ethyl acetate (10 ml.) add dropwise a solution of N,N-dicyclohexylcarbodiimide (0.50 gms.) in dichloromethane (5 ml.). Stir the mixture overnight with the exclusion of moisture. Filter the reaction mixture and wash the insoluble with ethyl acetate. Evaporate the combined filtrate and ethyl acetate washings in vacuo at 30° C. Dissolve the resultant residue comprising N-(S-γ-benzyloxycarbonylamino-α-hydroxybutyryloxy)succinimide in dry tetrahydrofuran (15 ml.).

(2) To a stirred solution of 3',6'-di-N-benzyloxycarbonyl-2'-hydroxy-2'-desaminogentamicin $C_{1a}$ prepared in Example 2A in methanol (12 ml.) and water (1.2 ml.) add 10 ml. of the tetrahydrofuran solution of N-[S-γ-(benzyloxycarbonylamino)-α-hydroxybutyryloxy]succinimide prepared in Example 2B(1) and stir the reaction mixture for 30 minutes, then add ammonium hydroxide (2 N; 10 ml.) and evaporate the reaction mixture in vacuo to remove methanol and tetrahydrofuran. Extract the resultant residue with chloroform, dry the combined extracts over potassium carbonate, filter and evaporate. Chromatograph the resultant residue on silica gel (70 gms.) eluting with solvent mixture comprising chloroform:methanol:concentrated ammonium hydroxide (12:1:0.1). Combine the like eluates containing the desired product as determined by thin layer chromatography, evaporate and dry the resultant residue in vacuo at 60° C. to obtain 3,6'-di-N-benzyloxycarbonyl-1-N-[S-γ-(benzyloxycarbonylamino)-α-hydroxyburyryl]-2'-hydroxy-2'-desaminogentamicin $C_{1a}$ as a white solid, yield 450 mg.; 32% theory; m.p. 200°-202° C.; $[\alpha]_D^{26}$ +51.1° (tetrahydrofuran, c=0.43). Combustion Analysis: Found: C, 57.2; H, 6.55; N, 6.9. Theory: $C_{47}H_{63}N_5O_{16} \cdot 2H_2O$ req C, 57.0; H, 6.8; N, 7.1%.

C.

1-N-(S-γ-Amino-α-Hydroxybutyryl)-2'-Hydroxy-2'-Desamino-Gentamicin $C_{1a}$ (1-N-(S-γ-amino-α-hydroxybutyryl)-3',4'-Dideoxygentamicin B)

To 3,6'-di-N-benzyloxycarbonyl-1-N-[S-γ-(benzyloxycarbonylamino)-α-hydroxybutyryl]-2'-hydroxy-2'-desaminogentamicin $C_{1a}$ (400 mg.) in tetrahydrofuran (30 ml.) and water (4 ml.) add acetic acid (0.25 ml.) and 5% palladium-on-carbon (500 mg.) and shake the reaction mixture at one atmosphere of hydrogen for 24 hours. Dilute the reaction mixture with water, separate the catalyst by filtration and wash with 2 N ammonium hydroxide. Evaporate the combined filtrate and washings in vacuo, dissolve the resultant residue in water and pass down a column of IRA-401S (OH⊖) resin eluting slowly with water. Collect the eluates under nitrogen, combine the like eluates containing the desired product as determined by thin layer chromatography and lyophilize the combined eluates to obtain 1-N-(S-γ-amino-α-hydroxybutyryl)-2'-hydroxy-2'-desaminogentamicin $C_{1a}$ as a white amorphous solid, yield 156 mg., 70% theory; m.p. 70°-80° C.; $[\alpha]_D^{26}$ +109.5° (water, c=0.25). pmr in $D_2O$ 1.17 (s, 3,4″—$CCH_3$), 2.47 (s, 3,3″—$NCH_3$), 4.08 (d, $J_5″ax_5″eq$=13 Hz, 1, $H_5″eq$), 4.18 (dd, 1, $H_2'''$), 5.09 (d, $JH_1″2″$=4 Hz, 1, $H_1″$) and 5.29 (dd, $H_1'2'$=4 Hz, 1, $H_1'$).

D.

1-N-(S-β-Amino-α-hydroxypropionyl)-2'-Hydroxy-2'-Desamino-Gentamicin $C_{1a}$ (1-N-(S-β-amino-α-Hydroxypropionyl)-3',4'-Dideoxygentamicin B)

Prepare a solution of N-[S-β-(benzyloxycarbonylamino)-α-hydroxypropionyloxy]succinimide in tetrahydrofuran from S-β-(benzyloxycarbonylamino)-α-hydroxypropionic acid and dry N-hydroxy-succinimide in a manner similar to that described in Example 2B(1) and add dropwise to a solution of 3,6'-di-N-benzyloxycarbonyl-2'-hydroxy-2'-desaminogentamicin $C_{1a}$ in aqueous methanol and isolate and purify the resultant product in a manner similar to that described in Example 2B(2) to obtain 3,6'-di-N-benzyloxycarbonyl-1-N-[S-β-(benzyloxycarbonylamino)-α-hydroxypropionyl]-2'-hydroxy-2'-desaminogentamicin $C_{1a}$. Hydrogenate the foregoing 3',6'-di-N-benzyloxycarbonyl derivative in aqueous tetrahydrofuran in the presence of palladium-on-carbon in a manner similar to that described in Example 2C to obtain 1-N-(S-β-amino-α-hydroxypropionyl)-2'-hydroxy-2'-desaminogentamicin $C_{1a}$.

E.

1-N-(S-δ-Amino-α-hydroxyvaleryl)-2'-Hydroxy-2'-Desamino-Gentamicin $C_{1a}$ (1-N-(S-δ-amino-α-hydroxyvaleryl)-3',4'-Dideoxygentamicin B)

In a manner similar to that described in Example 2B(1), prepare a solution of N-[S-δ-(benzyloxycarbonylamino)-α-hydroxyvaleryl]succinimide in tetrahydrofuran from S-δ-benzyloxycarbonylamino-α-hydroxyvaleric acid and dry N-hydroxysuccinimide, then add this solution dropwise to a solution of 3',6'-di-N-benzyloxycarbonyl-2'-hydroxy-2'-desaminogentamicin $C_{1a}$ in aqueous methanol in a manner similar to that described in Example 2B(2). Isolate and purify the resultant product in a manner similar to that described to obtain 3,6'-di-N-benzyloxycarbonyl-1-N-[S-δ-(benzyloxycarbonylamino)-α-hydroxyvaleryl]-2'-hydroxy-2'-desaminogentamicin $C_{1a}$. Hydrogenate the foregoing 3',6'-di-N-benzyloxycarbonyl derivative in aqueous tetrahydrofuran in the presence of palladium-on-carbon in a manner similar to that described in Example 2C to obtain 1-N-(S-δ-amino-α-hydroxyvaleryl)-2'-hydroxy-2'-desaminogentamicin $C_{1a}$.

EXAMPLE 3

2'-HYDROXY-2'-DESAMINOSISOMICIN

A.
1,3,6'-Tri-N-Benzoyl-3''-N-Acetyl-2'-Oximino-2'-Desaminosisomicin

Stir a solution of 1,3,6'-tri-N-benzoyl-3''-N-acetylsisomicin (8.9 gms.) in methanol (130 ml.) and water (10 ml.) with aqueous hydrogen peroxide (50%, 4 ml.), then add a solution of sodium tungstate (0.25 gms.) in water (3 ml.). Stir the reaction mixture at room temperature maintaining a pH of about 9-10 by periodic small additions of aqueous sodium hydroxide solution (10% w/v). After 3 hours, add additional hydrogen peroxide (1 ml.) and sodium tungstate (0.12 gms.) and stir the reaction mixture overnight at room temperature. Add acetic acid (2 ml.) to the reaction mixture, then pour the mixture into water (1 liter). Decant the aqueous mixture from the solid residue, rinse the solid residue with water and retain the residue. Combine the aqueous mixture with the water washings and extract with a chloroform:isopropanol (4:1) solvent mixture (three portions of 300 ml.). Dissolve the original solid residue in the combined organic solvent extracts, dry the solution over sodium carbonate, filter and evaporate. Chromatograph the resultant residue on silica gel (200 gms.) eluting with a solvent mixture comprising chloroform:methanol:ammonium hydroxide (10:1:0.1). Combine the like fractions containing the desired product as determined by thin layer chromatography and evaporate to a residue comprising 1,3,6'-tri-N-benzoyl-3''-N-acetyl-2'-oximino-2'-desaminosisomicin, yield 3.1 gms., which is used without further purification in the procedure of following Example 3B.

B. 2'-Hydroxy-2'-Desaminosisomicin

To a stirred solution of 1,3,6'-tri-N-benzoyl-3''-N-acetyl-2'-oximino-2'-desaminosisomicin prepared in Example 3A (3.1 gms.) in ethanol (50 ml.) and water (20 ml.), add sodium bisulfite (5 gms.) and stir at reflux temperature for 1 hour. Add acetic acid (6 ml.) and water (15 ml.) and subject the solution to slow distillation for 15 minutes, then cool. To the cooled solution containing 1,3,6'-tri-N-benzoyl-3''-N-acetyl-2'-oxo-2'-desaminosisomicin, add sodium carbonate (7.5 gms.) in small portions with stirring followed by sodium borohydride (1.7 gms.) in small portions. Stir the reaction mixture overnight, then dilute with isopropanol (400 ml.), filter, wash the insoluble salts with isopropanol, then evaporate the combined filtrate and washings in vacuo to a residue comprising 1,3,6'-tri-N-benzoyl-3''-N-acetyl-2'-hydroxy-2'-desaminosisomicin.

To the foregoing residue add a solution of sodium hydroxide (7 gms.) in water (50 ml.) and heat at reflux temperature under an atmosphere of argon for 60 hours. Cool, add dilute sulfuric acid until the solution is at a pH of about 10 and pour onto excess IRC-50 (H⊕) resin. Wash the resin with water, then elute with an excess of 1 N ammonium hydroxide. Evaporate the combined eluates and chromatograph the resultant residue on silica gel (100 gms.) eluting with the lower phase of a chloroform:methanol:15% ammonium hydroxide (2:1:1) solvent mixture. Evaporate the combined, like fractions containing the desired product as determined by thin layer chromatography, dissolve the resultant residue in water and pass through a short column of IRA-401S (OH⊖) resin. Elute with water and lyophilize the eluates to obtain 2'-hydroxy-2'-desaminosisomicin as a white amorphous solid.

EXAMPLE 4

1-N-(AMINOHYDROXYALKANOYL)-2'-HYDROXY-2'-DESAMINOSISOMICIN

A.
3,6'-Di-N-Benzyloxycarbonyl-2'-Hydroxy-2'-Desaminogentamicin $C_{1a}$ In a manner similar to that described in Example 2A, treat 2'-hydroxy-2'-desaminosisomicin in dimethylsulfoxide with cupric acetate and nickelous acetate followed by treatment with N-(benzyloxycarbonyloxy)phthalimide, and then reaction with aqueous ammonium hydroxide. Isolate and purify the resultant product in a manner similar to that described to obtain 3,6'-di-N-benzyloxycarbonyl-2'-hydroxy-2'-desaminosisomicin.

B.
3,6'-Di-N-Benzyloxycarbonyl-1-N-(S-Benzyloxycarbonylamino-α-Hydroxyalkanoyl)-2'-Hydroxy-2'-Desaminosisomicin In a manner similar to that described in Examples 2B(2), 2C and 2D, treat a solution of 3,6'-di-N-benzyloxycarbonyl-2'-hydroxy-2'-desaminosisomicin in aqueous methanol with each of N-[S-γ-(benzyloxycarbonylamino)-α-hydroxybutyryloxy]succinimide, N-[S-β-(benzyloxycarbonylamino)-α-hydroxypropionyloxy]succinimide, and N-[S-δ-(benzyloxycarbonylamino)-α-hydroxyvaleryloxy]succinimide. Isolate and purify each of the resultant products in a manner similar to that described in Example 3B(2) to obtain, respectively, 3,6'-di-N-benzyloxycarbonyl-1-N-[S-γ-(benzyloxycarbonylamino)-α-hydroxybutyryl]-2'-hydroxy-2'-desaminosisomicin, 3,6'-di-N-benzyloxycarbonyl-1-N-[S-β-(benzyloxycarbonylamino)-α-hydroxypropyl]-2'-hydroxy-2'-desaminosisomicin, and 3,6'-di-N-benzyloxycarbonyl-1-N-[S-δ-(benzyloxycarbonylamino)-α-hydroxyvaleryl]-2'-hydroxy-2'-desaminosisomicin.

C.
1-N-Aminohydroxyalkanoyl-2'-Hydroxy-2'-Desaminosisomicin

In a manner similar to that described in Example 1D, treat a solution of each of the compounds prepared in Example 4B in tetrahydrofuran with sodium in liquid ammonia, then isolate and purify each of the resultant products in a manner similar to that described in Example 1D to obtain, respectively, 1-N-[S-γ-amino-α-hydroxybutyryl]-2'-hydroxy-2'-desaminosisomicin, 1-N-[S-β-amino-α-hydroxypropyl]-2'-hydroxy-2'-desaminosisomicin, and 1-N-[S-δ-amino-α-hydroxyvaleryl]-2'-hydroxy-2'-desaminosisomicin.

EXAMPLE 5

2'-HYDROXY-2'-DESAMINOGENTAMICIN C$_1$

A.
1,3,6',3''-Tetra-N-Ethoxycarbonyl-2'-Oximino-2'-Desaminogentamicin C$_1$ To a solution of 1,3,6',3''-tetra-N-ethoxycarbonylgentamicin C$_1$ (0.5 gms., 0.652 mmol) in methanol (6 ml.) add sodium tungstate dihydrate (21.5 mg.) in water (1 ml.), then add hydrogen peroxide (0.2 ml., 30% solution). Stir, add additional methanol to complete solution, adjust the pH from 4.8 to 7.8 by the dropwise addition of 2 N sodium hydroxide, then add additional sodium tungstate dihydrate (60 mg.) in water (1 ml.) and adjust the pH to 10.5 by the dropwise addition of 2 N sodium hydroxide. Continue stirring at room temperature for 2 hours. Extract the reaction mixture with chloroform (three portions of 75 ml.), dry over magnesium sulfate and evaporate in vacuo to a residue comprising 1,3,6',3''-tetra-N-ethoxycarbonyl-2'-oximinogentamicin C$_1$ (yield 0.3 gms.) which is used without further purification in the procedure of Example 5B.

B.
1,3,6',3''-Tetra-N-Ethoxycarbonyl-2'-Oxo-2'-Desaminogentamicin C$_1$

To a solution of 1,3,6',3''-tetra-N-ethoxycarbonyl-2'-oximino-2'-desaminogentamicin C$_1$ (0.1 gm.) in acetonitrile (0.3 ml.) add 1 N hydrochloric acid (0.28 ml.) containing acetaldehyde (0.02 ml.) followed by water (5 ml.). Extract the reaction mixture with ethyl acetate (three portions of 15 ml.), dry over magnesium sulfate and evaporate in vacuo to a residue comprising 1,3,6',3''-tetra-N-ethoxycarbonyl-2'-oxo-2'-desaminogentamicin C$_1$ (yield 80 mg.) which is used without further purification in the procedure of Example 5C.

C.
1,3,6',3''-Tetra-N-Ethoxycarbonyl-2'-Hydroxy-2'-Desaminogentamicin C$_1$ To a solution of 1,3,6',3''-tetra-N-ethoxycarbonyl-2'-oxo-2'-desaminogentamicin C$_1$ (80 mg.) in dioxane (2 ml.) and water (2 ml.) at 0° C. with stirring add dropwise a solution of sodium borohydride (50 mg.) in aqueous dioxane (1:1, 2 ml.). Add acetone (3 ml.) followed by water (5 ml.). Extract with ethyl acetate (three portions of 15 ml.), dry over magnesium sulfate and evaporate in vacuo to a residue comprising 1,3,6',3''-tetra-N-ethoxycarbonyl-2'-hydroxy-2'-desaminogentamicin C$_1$, which is used without further purification in the procedure of following Example 5D.

D. 2'-Hydroxy-2'-Desaminogentamicin C$_1$

To a solution of 1,3,6',3''-tetra-N-ethoxycarbonyl-2'-hydroxy-2'-desaminogentamicin C$_1$ (1.21 gms.) in dimethylsulfoxide (16 ml.) add a solution of potassium hydroxide (2 gms.) in water (3 ml.) at 25° C. Stir at room temperature for 16 hours, then add 2 N sulfuric acid dropwise until the solution is at about pH 10.5. Filter, dilute the reaction solution with water (50 ml.), then add IR-50 (H⊕) resin until the reaction mixture is at pH 5. Filter the resin, wash the resin with water (200 ml.) discarding the water washing. Wash the resin with 2 N ammonium hydroxide and evaporate the ammonium hydroxide solution in vacuo. Dissolve the resultant residue in 10% aqueous sodium hydroxide (5 ml.) and heat in a teflon bomb for 16 hours at 80° C., then for 16 hours at 120° C. Acidify the reaction mixture to a pH of about 11 with 2 N sulfuric acid, filter, then add IR-50 (H⊕) resin until the reaction mixture is at a pH of about 4.5. Filter, wash the resin with water, discarding the water wash, then wash the resin with 2 N ammonium hydroxide. Evaporate the ammonium hydroxide wash in vacuo, dissolve the resultant residue in 90% hydrazine hydrate and heat at reflux temperature for 16 hours. Evaporate, chromatograph the resultant residue over silica gel eluting with a solvent mixture comprising chloroform:isopropanol:17% ammonium hydroxide (2:1:1). Combine the like eluates containing the desired product as determined by thin layer chromatography and evaporate to a residue of 2'-hydroxy-2'-desaminogentamicin C$_1$; 479 (M+1)$^+$, 478 (M.$^+$), 421, 348, 330, 320, 302, 350, 332, 322, 304, 160, 158. PMR (100 MHz, D$_2$O) δ0.97 (3H, d, J=6.3 Hz, $\underline{CH_3}$—CH), 1.14 (3H, s, $\underline{CH_3}$—C$_4$''), 2.24 (3H, s, $\underline{CH_3}$—N), 2.43 (3H, s, $\underline{CH_3}$—N), 3.27 (1H, d, J=12.5 Hz, H-5'' ax), 3.73 (1H, q, J=4, 10 Hz, H-2''), 3.99 (1H, d, J=12.5 Hz, 5'' eq), 5.01 (1H, d, J=4, H-1''), 5.12 (1H, d, J=3.5, H-1') ppm.

EXAMPLE 6

1-N-(AMINOHYDROXYALKANOYL)-2'-HYDROXY-2'-DESAMINOGENTAMICIN C$_1$

A.
3,6'-Di-N-Benzyloxycarbonyl-2'-Hydroxy-2'-Desaminogentamicin C$_1$

To a solution of 2'-hydroxy-2'-desaminogentamicin C$_1$ (0.79) in dimethylsulfoxide (31.6 ml.), add cupric acetate dihydrate (490 mg.) and nickelous acetate tetrahydrate (6.16 mg.). Stir until solution is complete, then add N-(benzyloxycarbonyloxy)phthalimide (1.147 gms.). Follow the course of the reaction via thin layer chromatography, adding 2 additional 50 mg. portions of N-(benzyloxycarbonyloxy)phthalimide at intervals. When one new major spot has appeared on the thin layer chromatogram, add 2 N ammonium hydroxide (250 ml), extract with methylene chloride (eight portions of 100 ml.), wash the methylene chloride extracts with water, then dry over magnesium sulfate and evaporate in vacuo to a residue comprising 3,6'-di-N-benzyloxycarbonyl-2'-hydroxy-2'-desaminogentamicin C$_1$, which is used without further purification in the procedure of Example 6B.

B.
3,6'-Di-N-Benzyloxycarbonyl-1-N-[S-β-(benzyloxycarbonylamino)-α-Hydroxypropionyl]-2'-Hydroxy-2'-Desaminogentamicin C$_1$ To a solution of the 3,6'-di-N-benzyloxycarbonyl-2'-hydroxy-2'-desaminogentamicin C$_1$ prepared in Example 6A in methanol (20 ml.) and water (2 ml.), with stirring add N-(S-β-benzyloxycarbonylamino-α-propionyloxy)succinimide (1.5 equivalents in three equal portions). Extract with methylene chloride (three portions of 150 ml.), dry over magnesium sulfate, and evaporate, chromatograph the resultant residue over silica gel (40 gms.) eluting with a solvent mixture comprising chloroform:methanol:ammonium hydroxide (2:1:1). Combine the like fractions ontaining the desired product as determined by thin layer chromatography and evaporate the combined eluates in vacuo to a residue comprising 3,6'-di-N-benzyloxycarbonyl-1-N-[S-β-(benzyloxycarbonylamino)-α-hydroxypropionyl]-2'- hydroxy-2'-desaminogentamicin $C_1$, yield 0.34 gms. Combustion Analysis: Found: C, 58.93; H, 6.48; N, 7.08. Theory: $C_{48}H_{65}N_5O_{16} \cdot H_2O$ C, 59.01; H, 6.81; N, 7.17.

C.

1-N-(S-β-Amino-α-Hydroxypropionyl)-2'-Hydroxy-2'-Desaminogentamicin $C_1$

To a solution of 3,6'-di-N-benzyloxycarbonyl-1-N-[S-β-(benzyloxycarbonylamino)-α-hydroxypropionyl]-2'-hydroxy-2'-desaminogentamicin $C_1$ (0.3 gms.) in aqueous tetrahydrofuran (1:10) (15 ml.), add acetic acid (0.15 ml.) and hydrogenate in the presence of 5% palladium-on-charcoal (200 mg.) at 60 psc for 16 hours. Filter, evaporate the filtrate and chromatograph the resultant residue over silica gel (2 gms.) eluting with a solvent mixture comprising chloroform:methanol:ammonium hydroxide (3:4:2). Combine the like eluates containing the desired product as determined by thin layer chromatography and evaporate in vacuo to a residue comprising 1-N-(S-β-amino-α-hydroxypropionyl)-2'-hydroxy-2'-desaminogentamicin $C_1$. Further purify by dissolving in water, pouring the aqueous solution over IRA-401S ($OH^-$) resin (0.6 ml.) eluting slowly with water. Collect the eluates under nitrogen and freeze dry the combined eluates to obtain 1-N-(S-γ-amino-α-hydroxypropionyl)-2'-hydroxy-2'-desaminogentamicin $C_1$, yield 75.7 mg., $[\alpha]_D^{26} + 99.7°$ (water, c=0.32). Combustion Analysis: C, 46.73; H, 7.81; N, 10.74. Calculated $C_{24}H_{47}N_5O_{16} \cdot 1.5 H_2CO_3$, C, 46.5; H, 7.65; N, 10.63; PMR (100 MHz, $D_2O$) δ0.99 (3H, d, J=6.8 Hz, $CH_3$—CH), 1.13 (3H, s, $CH_3$—$C_4''$), 2.27 (3H, s, $CH_3$—N), 2.43 (3H, s, $CH_3$-N), 5.03 (1H, d, J=3.5, H-1''), 5.15 (1H, d, J=3.7 Hz, H-1') ppm.

D. In a manner similar to that described in Example 6B, treat 3,6'-di-N-benzyloxycarbonyl-2'-hydroxy-2'-desaminogentamicin $C_1$ with each of N-(S-γ-benzyloxycarbonylamino-α-hydroxybutyryloxy)succinimide and N-(S-δ-benzyloxycarbonylamino-α-hydroxyvaleryloxy)succinimide and isolate and purify each of the resultant products in the described manner to obtain 3,6'-di-N-benzyloxycarbonyl-1-N-(S-γ-amino-α-hydroxybutyryl)-2'-hydroxy-2'-desaminogentamicin $C_1$ and 3,6'-di-N-benzyloxycarbonyl-1-N-(S-δ-amino-α-hydroxyvaleryl)-2'-hydroxy-2'-desaminogentamicin $C_1$, respectively. Hydrogenate each of the foregoing products in the presence of 5% palladium-on-charcoal in a manner similar to that described in Example 6C and isolate and purify each of the resultant products to obtain, respectively, 1-N-(S-γ-amino-α-hydroxybutyryl)-2'-hydroxy-2'-desaminogentamicin $C_1$ and 1-N-(S-δ-amino-α-hydroxyvaleryl)-2'-hydroxy-2'-desaminogentamicin $C_1$.

EXAMPLE 7

OTHER 2'-HYDROXY-2'-DESAMINO AMINOGLYCOSIDES

A. Subject each of the 1,3,6',3''-tetra-N-benzyloxycarbonylaminoglycoside derivatives prepared in Preparations 6 and 7 to a series of reactions similar to that described in Examples 1A-1D to obtain, respectively, 2'-hydroxy-2'-desaminotobramycin, 2'-hydroxy-2'-desaminogentamicin $C_2$, 2'-hydroxy-2'-desaminogentamicin $C_{2a}$, 2'-hydroxy-2'-desamino-3',4'-dideoxykanamycin A (also named 3',4'-dideoxy-kanamycin A), 2'-hydroxy-2'-desamino-Antibiotic JI-20A (also named gentamicin B), and 2'-hydroxy-2'-desamino-Antibiotic JI-20B.

B. Subject 1,3,6',3''-tetra-N-ethoxycarbonylgentamicin $C_{2b}$ to a series of reactions similar to that described in Examples 5A–5D and isolate and purify the resultant product in a manner similar to that in Example 5D to obtain 2'-hydroxy-2'-desaminogentamicin $C_{2b}$.

C. Subject each of the 1,3,6'-tri-N-benzoyl-3''-N-acetylaminoglycoside derivatives prepared in Preparation 5 to a series of reactions similar to those described in Example 3, and isolate and purify each of the resultant products in a manner similar to that described in Example 3B to obtain, respectively, 2'-hydroxy-2'-desamino-Antibiotic G-52, 2'-hydroxy-2'-desamino-Antibiotic 66-40D, 2'-hydroxy-2'-desamino-Antibiotic 66-40B, 2'-hydroxy-2'-desaminoverdamicin, 2'-hydroxy-2'-desamino-Antibiotic Mu-1, 2'-hydroxy-2'-desamino-5-deoxysisomicin, 2'-hydroxy-2'-desamino-Antibiotic Mu-4, 2'-hydroxy-2'-desamino-5-episisomicin, 2'-hydroxy-2'-desamino-5-epi-azido-5-deoxysisomicin, and 2'-hydroxy-2'-desamino-1-N-ethylsisomicin.

EXAMPLE 8

1-N-(ω-AMINO-α-HYDROXYALKANOYL)-2'-HYDROXY-2'-DESAMINO AMINOGLYCOSIDE DERIVATIVES

A.

3,6'-Di-N-Benzyloxycarbonyl-2'-Hydroxy-2'-Desamino Aminoglycoside

In a manner similar to that described in Example 2A, treat each of the 2'-hydroxy-2'-desamino aminoglycosides prepared in Examples 7A, 7B and 7C with powdered cupric acetate and nickelous acetate followed by treatment with N-(benzyloxycarbonyloxy)phthalimide. Isolate and purify each of the resultant products in a manner similar to that described to obtain the corresponding 3',6'-di-N-benzyloxycarbonyl derivative.

B.

3,6'-Di-N-Benzyloxycarbonyl-1-N-[S-ω-(benzyloxycarbonylamino)-α-Hydroxyalkanoyl]-2'-Hydroxy-2'-Desamino Aminoglycosides (1)

3,6'-Di-N-Benzyloxycarbonyl-1-N-[S-γ-(benzyloxycarbonylamino)-α-Hydroxybutyryl]-2'-Hydroxy-2'-Desamino Aminoglycosides In a manner similar to that described in Example 2B(2), treat each of the 3,6'-di-N-benzyloxycarbonyl-2'-hydroxy-2'-desamino aminoglycosides prepared in Example 8A with N-(S-γ-benzyloxycarbonylamino-α-hydroxybutyryloxy)succinimide, then isolate and purify each of the resultant products in a manner similar to that described to obtain the corresponding 1-N-[S-γ-(benzyloxycarbonylamino)-α-hydroxybutyryl] derivative.

(2)

3,6'-Di-N-Benzyloxycarbonyl-1-N-[S-β-(benzyloxycarbonylamino)-α-hydroxypropionyl]-2'-Hydroxy-2'-Desamino Aminoglycosides In a manner similar to that described in Examples 2D and 6B, treat each of the 3,6'-di-N-benzyloxycarbonyl-2'-hydroxy-2'-desamino aminoglycosides prepared in Examples 7A, 7B and 7C with N-(S-β-benzyloxycarbonylamino-α-hydroxypropionyloxy)succinimide and isolate and purify each of the resultant products in a manner similar to that described to obtain 1-N-[S-β-(benzyloxycarbonylamino)-α-hydroxypropionyl] derivative.

(3)

3,6'-Di-N-benzyloxycarbonyl-1-N-[S-δ-(benzyloxycarbonylamino)-α-Hydroxyvaleryl]-2'-Hydroxy-2'-Desamino Aminoglycosides In a manner similar to that described in Example 2E, treat each of the 3,6'-di-N-benzyloxycarbonyl-2'-hydroxy-2'-desamino aminoglycoside derivatives prepared in Examples 7A, 7B and 7C with N-(S-δ-benzyloxycarbonylamino-α-hydroxyvaleryl)succinimide and isolate and purify each of the resultant products in a manner similar to that described to obtain, respectively, the 1-N-[S-δ-(benzyloxycarbonylamino)-α-hydroxyvaleryl] derivative.

C.

1-N-(S-ω-Amino-α-Hydroxyalkanoyl)-2'-Hydroxy-2'-Desamino Aminoglycosides (1) In a manner similar to that described in Example 2C, hydrogenate each of the 3,6'-di-N-benzyloxycarbonyl-1-N-[S-ω-(benzyloxycarbonylamino)-α-hydroxyalkanoyl]-2'-hydroxy-2'-desamino aminoglycoside derivatives prepared in Example 8B(1), (2) and (3) which were derived from the products of Examples 7A and 7B, isolate and purify each of the resultant products in a manner similar to that in Example 2C to obtain, respectively, 1-N-(S-γ-amino-α-hydroxybutyryl)-2'-hydroxy-2'-desaminotobramycin, 1-N-(S-γ-amino-α-hydroxybutyryl)-2'-hydroxy-2'-desaminogentamicin $C_2$, 1-N-(S-γ-amino-α-hydroxybutyryl)-2'-hydroxy-2'-desaminogentamicin $C_{2a}$, 1-N-(S-γ-amino-α-hydroxybutyryl)-2'-hydroxy-2'-desamino-3',4'-dideoxykanamycin B, 1-N-(S-γ-amino-α-hydroxybutyryl)-2'-hydroxy-2'-desaminogentamicin $C_{2b}$; 1-N-(S-β-amino-α-hydroxypropionyl)-2'-hydroxy-2'-desaminotobramycin, 1-N-(S-β-amino-α-hydroxypropionyl)-2'-hydroxy-2'-desaminogentamicin $C_2$, 1-N-(S-β-amino-α-hydroxypropionyl)-2'-hydroxy-2'-desaminogentamicin $C_{2a}$, 1-N-(S-β-amino-α-hydroxypropionyl)-2'-hydroxy-2'-desamino-3',4'-dideoxykanamycin B, 1-N-(S-β-amino-α-hydroxypropionyl)-2'-hydroxy-2'-desaminogentamicin $C_{2b}$; 1-N-(S-δ-amino-α-hydroxyvaleryl)-2'-hydroxy-2'-desaminotobramycin, 1-N-(S-δ-amino-α-hydroxyvaleryl)-2'-hydroxy-2'-desaminogentamicin $C_2$, 1-N-(S-δ-amino-α-hydroxyvaleryl)-2'-hydroxy-2'-desaminogentamicin $C_{2a}$, 1-N-(S-δ-amino-α-hydroxyvaleryl)-2'-hydroxy-2'-desamino-3',4'-dideoxykanamycin B, 1-N-(S-δ-amino-α-hydroxyvaleryl)-2'-hydroxy-2'-desaminogentamicin $C_{2b}$.

(2) In a manner similar to that described in Example 1D, treat each of the 3,6'-di-N-benzyloxycarbonyl-1-N-[S-ω-(benzyloxycarbonylamino)-α-hydroxyalkanoyl]-2'-hydroxy-2'-desamino aminoglycosides prepared in Example 8B(1), (2), and (3) which were derived from the products of Example 7C with sodium in liquid ammonia. Isolate and purify each of the resultant products in a manner similar to that described to obtain, respectively, 1-N-(S-γ-amino-α-hydroxybutyryl)-2'-hydroxy-2'-desamino-Antibiotic G-52, 1-N-(S-γ-amino-α-hydroxybutyryl)-2'-hydroxy-2'-desamino-Antibiotic 66-40D, 1-N-(S-γ-amino-αhydroxybutyryl)-2'-hydroxy-2'-desamino-Antibiotic 66-40B, 1-N-(S-γ-amino-α-hydroxybutyryl)-2'-hydroxy-2'-desaminoverdamicin, 1-N-(S-γ-amino-α-hydroxybutyryl)-2'-hydroxy-2'-desamino-Antibiotic Mu-1, 1-N-(S-γ-amino-α-hydroxybutyryl)-2'-hydroxy-2'-desamino-5-deoxysisomicin, 1-N-(S-γ-amino-α-hydroxybutyryl)-2'-hydroxy-2'-desamino-Antibiotic Mu-4, 1-N-(S-γ-amino-α-hydroxybutyryl)-2'-hydroxy-2'-desamino-5-episisomicin, 1-N-(S-γ-amino-α-hydroxybutyryl)-2'-hydroxy-2'-desamino-5-epi-azido-5-deoxysisomicin, and 1-N-(S-γ-amino-α-hydroxybutyryl)-2'-hydroxy-2'-desamino-1-N-ethylsisomicin; 1-N-(S-β-amino-α-hydroxypropionyl)-2'-hydroxy-2'-desamino-Antibiotic G-52, 1-N-(S-β-amino-α-hydroxypropionyl)-2'-hydroxy-2'-desamino-Antibiotic 66-40D, 1-N-(S-β-amino-α-hydroxypropionyl)-2'-hydroxy-2'-desamino-Antibiotic 66-40B, 1-N-(S-β-amino-α-hydroxypropionyl)-2'-hydroxy-2'-desaminoverdamicin, 1-N-(S-β-amino-α-hydroxypropionyl)-2'-hydroxy-2'-desamino-Antibiotic Mu-1, 1-N-(S-β-amino-α-hydroxypropionyl)-2'-hydroxy-2'-desamino-5-deoxysisomicin, 1-N-(S-β-amino-α-hydroxypropionyl)-2'-hydroxy-2'-desamino-Antibiotic Mu-4, 1-N-(S-β-amino-α-hydroxypropionyl)-2'-hydroxy-2'-desamino-5-episisomicin, 1-N-(S-β-amino-α-hydroxypropionyl)-2'-hydroxy-2'-desamino-5-epi-azido-5-deoxysisomicin, and 1-N-(S-β-amino-α-hydroxypropionyl)-2'-hydroxy-2'-desamino-1-N-ethylsisomicin; 1-N-(S-δ-amino-α-hydroxyvaleryl)-2'-hydroxy-2'-desamino-Antibiotic G-52, 1-N-(S-δ-amino-α-hydroxyvaleryl)-2'-hydroxy-2'-desamino-Antibiotic 66-40D, 1-N-(S-δ-amino-α-hydroxyvaleryl)-2'-hydroxy-2'-desamino-Antibiotic 66-40B, 1-N-(S-δ-amino-α-hydroxyvaleryl)-2'-hydroxy-2'-desaminoverdamicin, 1-N-(S-δ-amino-α-hydroxyvaleryl)-2'-hydroxy-2'-desamino-Antibiotic Mu-1, 1-N-(S-δ-amino-α-hydroxyvaleryl)-2'-hydroxy-2'-desamino-5-deoxysisomicin, 1-N-(S-δ-amino-α-hydroxyvaleryl)-2'-hydroxy-2'-desamino-Antibiotic Mu-4, 1-N-(S-δ-amino-α-hydroxyvaleryl)-2'-hydroxy-2'-desamino-5-episisomicin, 1-N-(S-δ-amino-α-hydroxyvaleryl)-2'-hydroxy-2'-desamino-5-epi-azido-5-deoxysisomicin, and 1-N-(S-δ-amino-α-hydroxyvaleryl)-2'-hydroxy-2'-desamino-1-N-ethylsisomicin.

EXAMPLE 9

ACID ADDITION SALTS

A. Sulfate Salts (Sulfuric Acid Addition Salts)

Dissolve 5.0 gms. of 2'-hydroxy-2'-desaminogentamicin $C_{1a}$ in 25 ml. of water and adjust the pH of the solution to 4.5 with 1 N sulfuric acid. Pour into about 300 ml. of methanol with vigorous agitation, continue the agitation for about 10–20 minutes and filter. Wash the precipitate with methanol and dry at about 60° C. in vacuo to obtain 2'-hydroxy-2'-desaminogentamicin $C_{1a}$ sulfate.

In like manner, the sulfate salt of the compounds of Examples 2 to 8 are prepared.

B. Hydrochloride Salts

Dissolve 5.0 gms. of 2'-hydroxy-2'-desaminogentamicin $C_{1a}$ in 25 ml. of water. Acidify with 2 N hydrochloric acid to pH 5. Lyophilize to obtain 2'-hydroxy-2'-desaminogentamicin $C_{1a}$ hydrochloride.

In like manner, the hydrochloride salt of the compounds of Examples 2 to 8 are prepared.

We claim:

1. A 2'-hydroxy-2'-desamino-4,6-di-O-(aminoglycosyl)-1,3-diaminocyclitol having an amino function at C-6' selected from the group consisting of 2'-hydroxy-2'-desaminogentamicin $C_1$,
2'-hydroxy-2'-desaminogentamicin $C_{1a}$,
2'-hydroxy-2'-desaminogentamicin $C_2$,
2'-hydroxy-2'-desaminogentamicin $C_{2a}$, 2'-hydroxy-2'-desaminogentamicin C$_{2b}$,
2'-hydroxy-2'-desaminosisomicin,
2'-hydroxy-2'-desaminoverdamicin,
2'-hydroxy-2'-desamino-Antibiotic G-52,
2'-hydroxy-2'-desamino-Antibiotic 66-40B,
2'-hydroxy-2'-desamino-Antibiotic 66-40D,
2'-hydroxy-2'-desamino-Antibiotic JI-20B,
2'-hydroxy-2'-desaminotobramycin; and
2'-hydroxy-2'-desamino-3',4'-dideoxykanamycin B;
the 5-deoxy-, 5-epi-, 5-epi-azido-5-deoxy derivatives thereof;
2'-hydroxy-2'-desamino-Antibiotic Mu-1 and
2'-hydroxy-2'-desamino-Antibiotic Mu-4;
the 1-N-($\omega$-amino-$\alpha$-hydroxyalkanoyl) derivatives of the foregoing wherein said alkanoyl has from 3 to 5 carbon atoms, and the 1-N-X derivatives of the foregoing wherein X is a substituent selected from the group consisting of alkyl, cycloalkylalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxl and amino functions, only one of said functions can be attached at any one carbon atom; and the pharmaceutically acceptable acid addition salts thereof.

2. A compound of claim 1 which is a 1-N-($\omega$-amino-$\alpha$-hydroxyalkanoyl) derivative of said 2'-hydroxy-2'-desamino-4,6-di-O-(aminoglycosyl)-1,3-diaminocyclitol.

3. A compound of claim 1 which is a 1-N-($\omega$-amino-$\alpha$-hydroxyalkanoyl) derivative of a 2'-hydroxy-2'-desamino-4-O-garosaminyl-2-deoxystreptamine of claim 1.

4. A compound of claim 3 wherein said 1-N-($\omega$-amino-$\alpha$-hydroxyalkanoyl) derivative is a 1-N-($\beta$-amino-$\alpha$-hydroxypropionyl) derivative.

5. A compound of claim 4 which is 1-N-(S-$\beta$-amino-$\alpha$-hydroxypropionyl)-2'-hydroxy-2'-desaminogentamicin C$_1$.

6. A compound of claim 4 which is 1-N-(S-$\beta$-amino-$\alpha$-hydroxypropionyl)-2'-hydroxy-2'-desaminogentamicin C$_{1a}$.

7. A compound of claim 3 wherein said 1-N-($\omega$-amino-$\alpha$-hydroxyalkanoyl) derivative is a 1-N-($\gamma$-amino-$\alpha$-hydroxybutyryl) derivative.

8. A compound of claim 7 which is 1-N-(S-$\gamma$-amino-$\alpha$-hydroxybutyryl)-2'-hydroxy-2'-desaminogentamicin C$_1$.

9. A compound of claim 7 which is 1-N-(S-$\gamma$-amino-$\alpha$-hydroxybutyryl)-2'-hydroxy-2'-desaminogentamicin C$_{1a}$.

10. The method of eliciting an antibacterial response in a warm-blooded animal having a susceptible bacterial infection which comprises administering to said animal a non-toxic, antibacterially effective amount of a 2'-hydroxy-2'-desamino-4,6-di-O-(aminoglycosyl)-1,3-diaminocyclitol of claim 1.

11. The method of claim 10 when carried out with a 1-N-(S-$\omega$-amino-$\alpha$-hydroxyalkanoyl)-2'-hydroxy-2'-desamino-4,6-di-O-(aminoglycosyl)-1,3-diaminocyclitol of claim 1.

12. A pharmaceutical composition comprising an inert carrier and an antibacterially effective amount of a 2'-hydroxy-2'-desamino-4,6-di-O-(aminoglycosyl)-1,3-diaminocyclitol of claim 1.

13. A composition of claim 12 comprising an inert carrier and an antibacterially effective amount of a 1-N-(S-$\omega$-amino-$\alpha$-hydroxyalkanoyl)-2'-hydroxy-2'-desamino-4,6-di-O-(aminoglycosyl)-1,3-diaminocyclitol of claim 1.

14. The process which comprises the reaction of a 4,6-di-O-(aminoglycosyl)-1,3-diaminocyclitol wherein said 4-O-aminoglycosyl has an amino function at the 2' and 6' positions and said 6-O-aminoglycosyl has a hydroxyl group at the 2'' and 4''-positions and a 3''-amino function, and wherein all amino functions except the 2'-amino function are protected by a protecting group, Y;

with hydrogen peroxide in an aqueous lower alkanol in the presence of tungstate ion in a pH range of from about 9 to about 11, the molar quantity of hydrogen peroxide being at least twice the molar quantity of said 4,6-di-O-(aminoglycosyl)-1,3-diaminocyclitol;

thence cleavage of the oxime function in the 2'-oximino-4,6-di-O-(aminoglycosyl)-1,3-diaminocyclitol thereby formed by reaction thereof with sodium bisulfite followed by mild acid hydrolysis or by reaction thereof in an acidic hydrolytic medium in the presence of acetaldehyde;

followed by reaction the resulting 2'-oxo-4,6-di-O-(aminoglycosyl)-1,3-diaminocyclitol with an alkali metal borohydride;

thence removal of said protecting groups, Y, whereby is produced the corresponding 2'-hydroxy-2'-desamino-4,6-di-O-(aminoglycosyl)-1,3-diaminocyclitols.

15. The process of claim 14 wherein cleavage of the oxime function is carried out by the reaction of said 2'-oximino-4,6-di-O-(aminoglycosyl)-1,3-diaminocyclitol with sodium bisulfite followed by mild acid hydrolysis.

16. The process of claim 14 wherein said 4,6-di-O-(aminoglycosyl)-1,3-diaminocyclitol is devoid of unsaturated bonds, said protecting groups, Y, are groups susceptible to reductive cleavage or to basic hydrolysis, and said alkali metal borohydride is sodium borohydride.

17. The process of claim 14 wherein said 4,6-di-O-(aminoglycosyl)-1,3-diaminocyclitol having amino protecting groups, Y, is 1,3,6',3''-tetra-N-benzyloxycarbonylgentamicin C$_{1a}$ and wherein said protecting groups, Y, are removed by reductive cleavage by means of sodium in ammonia whereby is formed 2'-hydroxy-2'-desaminogentamicin C$_{1a}$.

18. The process of claim 14 wherein said 4,6-di-O-(aminoglycosyl)-1,3-diaminocyclitol having amino protecting groups, Y, is 1,3,6',3''-tetra-N-ethoxycarbonylgentamicin C$_1$ and wherein said protecting groups, Y, are removed by alkaline hydrolysis, whereby is formed 2'-hydroxy-2'-desaminogentamicin C$_1$.

19. The process of claim 14 wherein said 4,6-di-O-(aminoglycosyl)-1,3-diaminocyclitol having protecting groups, Y, is 1,3,6'-tri-N-benzoyl-3''-N-acetylsisomicin, and wherein said protecting groups are removed by alkaline hydrolysis whereby is formed 2'-hydroxy-2'-desaminosisomicin.

20. The process of claim 14 wherein said 4,6-di-O-(aminoglycosyl)-1,3-diaminocyclitol having protecting groups, Y, is 1,3,6',3''-tetra-N-benzyloxycarbonyl-Antibiotic JI-20A whereby is produced 2'-hydroxy-2'-desamino-Antibiotic JI-20A.

* * * * *

UNITED STATES PATENT AND TRADEMARK OFFICE
CERTIFICATE OF CORRECTION

PATENT NO. : 4,212,859

DATED : July 15, 1980

INVENTOR(S) : Peter J. L. Daniels et al

It is certified that error appears in the above-identified patent and that said Letters Patent are hereby corrected as shown below:

First page, column 1, under the title "Inventors: Peter J.L. Daniels, Cedar Grove; Stuart McCombie, West Orange; Tattanahalli L. Nagabhushan, Parsippany, all of N.J." should read---------"Inventors: Peter J.L. Daniels, Cedar Grove; Stuart McCombie, West Orange; Tattanahalli L. Nagabhushan, Parsippany, Jay Weinstein, Bloomfield, all of N.J.

Signed and Sealed this

Sixteenth Day of December 1980

[SEAL]

Attest:

SIDNEY A. DIAMOND

Attesting Officer

Commissioner of Patents and Trademarks